United States Patent
Prabhakar et al.

(10) Patent No.: US 9,221,911 B2
(45) Date of Patent: Dec. 29, 2015

(54) ANTI-CLTA4, ANTI-GLUT2 PROTEIN FOR THE TREATMENT OF TYPE 1 DIABETES

(71) Applicants: Bellur S. Prabhakar, Oak Brook, IL (US); Chenthamarakshan Vasu, Charleston, SC (US); Palash Bhattacharya, Chicago, IL (US)

(72) Inventors: Bellur S. Prabhakar, Oak Brook, IL (US); Chenthamarakshan Vasu, Charleston, SC (US); Palash Bhattacharya, Chicago, IL (US)

(*) Notice: Subject to any disclaimer, the term of this patent is extended or adjusted under 35 U.S.C. 154(b) by 95 days.

(21) Appl. No.: 13/843,123

(22) Filed: Mar. 15, 2013

(65) Prior Publication Data

US 2013/0236464 A1 Sep. 12, 2013

Related U.S. Application Data

(63) Continuation-in-part of application No. PCT/US2012/047378, filed on Jul. 19, 2012.

(60) Provisional application No. 61/509,316, filed on Jul. 19, 2011.

(51) Int. Cl.
*C07K 16/28* (2006.01)
*C07K 16/46* (2006.01)
*A61K 39/395* (2006.01)
*A61K 39/00* (2006.01)

(52) U.S. Cl.
CPC ............ *C07K 16/2866* (2013.01); *C07K 16/28* (2013.01); *C07K 16/2818* (2013.01); *C07K 16/468* (2013.01); *A61K 2039/505* (2013.01); *A61K 2039/507* (2013.01); *A61K 2039/54* (2013.01); *A61K 2039/545* (2013.01); *C07K 2317/31* (2013.01)

(58) Field of Classification Search
None
See application file for complete search history.

(56) References Cited

U.S. PATENT DOCUMENTS

| | | | |
|---|---|---|---|
| 2004/0202650 A1* | 10/2004 | Gribben et al. | 424/131.1 |
| 2005/0226875 A1 | 10/2005 | Gomez-Navarro et al. | |
| 2008/0233122 A1 | 9/2008 | Hanson et al. | |
| 2010/0330034 A1 | 12/2010 | Bigler et al. | |
| 2013/0136749 A1* | 5/2013 | Korman et al. | 424/144.1 |

FOREIGN PATENT DOCUMENTS

| WO | WO 0037504 A2 | 6/2000 |
|---|---|---|
| WO | WO 2005115419 A1 | 12/2005 |

OTHER PUBLICATIONS

Poirier et al., American Journal of Transplantation 2012; 12: 2630-2640.*
Mayo Foundation for Medical Education and Research, 2012, accessed at mayoclinic.com/health/type-1-diabetes/DS00329 on Sep. 13, 2012.*
Aly et al., Am. J. Therapeutics (2005) 12: 481-490.*
Michels (Seminars in Immunology 23 (2011) 214-219.*
Gillard (Expert Opin. Biol. Ther. (2011) 11(5): 609-621.*
Bluestone (Cold Spring Harb Perspect Biol 2012;4:a007542.*
von Herrath (Clinical and Experimental Immunology, 2013, 172: 186-202.*
Coppieters (Clinical Immunology (2013) 149, 345-355.*
Oxford dictionary (American English), 2014, 1 page.*
Thorens et al., "Regulated expression of GLUT2 in diabetes studied in transplanted pancreatic B Cells," Biochemical Society Transactions 684-7. (1994).
Teft et al., "Molecular Determinants of Inverse Agonis Activity of Biologicals Targeting CTLA-4," The Journal of Immunology 3631-37, (2007).
Karumuthil-Melethil et al., "Dendritic cell directed CTLA-4 engagement during pancreatic B-cell antigen presentation delays type 1 diabetes," J Immunol 184(12)6695-6708 (2010).
Fife et al., "Inhibition of T cell activation and autoimmune diabetes using a B cell surface-linked CTLA-4 agonist," The Journal of Clinical Investigation 116(8) 2252-61 (2006).
Li et al., "Enhanced Engagement of CTLA-4 Induces, Antigen-Specific CD4+CD25+Foxp3+ and CD4+CD25- TGF-B1+ Adaptive Regulatory T Cells+," J. Immunol 5191-5203, (2007).
Vasu et al., "Targeted engagement of CTLA-4 prevents autoimmune thyroiditis,," International Immunology 15(5) 641-54 (2003).
Chatenoud, Lucienne, "CD3-Specific Antibody-induced active tolerance: from bench to bedside," Nature Reviews Immunology, vol. 3, No. 2: 123-132 (2003).
Chung, Denise T et al., "Anti-thymocyte globulin (ATG) prevents autoimmune encephalomyelitis by expanding myelin antigen-specif Foxp3+ regulatory T cells," International Immunology, vol. 19, No. 8: 1003-1010 (2007).
International Search Report and Written Opinion for International Application No. PCT/US2012/047378, Mailed Oct. 19, 2012.
Bingley et al. "Proposed Guidelines on Screening for Risk of Type 1 Diabetes," Diabetes Care, 24(2):398 (2001).

* cited by examiner

*Primary Examiner* — Ilia Ouspenski
(74) *Attorney, Agent, or Firm* — McDonnell Boehnen Hulbert & Berghoff LLP

(57) ABSTRACT

The disclosure relates to a protein composed of a first polypeptide or polypeptide domain having a first specific binding activity for Cytotoxic T-lymphocyte Antigen 4 (CTLA-4) expressed on a T-cell cell surface and a second specific binding activity for Glucose Transporter 2 (GLUT2) or an extracellular ectodomain thereof expressed on a pancreatic β-cell surface, wherein binding of the first polypeptide or polypeptide domain to CTLA-4 induces a CTLA-4 specific agonist response in the T-cell, and binding of the second polypeptide or polypeptide domain to GLUT2 or an ectodomain thereof does not inhibit GLUT2 glucose transporter function, wherein said agonist response in the T-cell induces a response that reduces immunoreactivity against pancreatic β-cells.

9 Claims, 17 Drawing Sheets

SEQUENCE LISTING

<160> NUMBER OF SEQ ID NOS: 6

<210> SEQ ID NO 1
<211> LENGTH: 5
<212> TYPE: PRT
<213> ORGANISM: Artificial Sequence
<220> FEATURE:
<223> OTHER INFORMATION: Peptide linker

<400> SEQUENCE: 1

Gly Gly Gly Gly Ser
1               5

<210> SEQ ID NO 2
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 2
gcgccatatg aatgcacctc aagaggtaat aata                              34

<210> SEQ ID NO 3
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 3
gcgcggatcc ttaagaccag agcatagtga ctatgtg                           37

<210> SEQ ID NO 4
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 4
gcgcggatcc atcagaagac aagatcaccg g                                 31

<210> SEQ ID NO 5
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 5
gcgcgaattc tcacacactc tctgaagacg c                                 31

<210> SEQ ID NO 6
<211> LENGTH: 10
<212> TYPE: PRT
<213> ORGANISM: Artificial Sequence
<220> FEATURE:
<223> OTHER INFORMATION: BDC2.5 peptide

<400> SEQUENCE: 6

Tyr Val Arg Pro Leu Trp Val Arg Met Glu
1               5                   10

ANTI-CLTA4, ANTI-GLUT2 PROTEIN FOR THE TREATMENT OF TYPE 1 DIABETES

This application is a continuation-in-part of International Application No. PCT/US12/47378, filed Jul. 19, 2012, which claims the benefit of priority to U.S. Provisional Patent Application Ser. No. 61/509,316, filed Jul. 19, 2011, each application incorporated by reference herein in their entireties.

BACKGROUND OF THE INVENTION

Type-1 diabetes (T1D) is a chronic autoimmune disorder thought to be caused by autoreactive T-cells that participate in destruction of insulin-producing pancreatic β-cells in the islets of Langerhans. Complete destruction of β-cells results in a lifelong dependence on exogenous insulin. Specifically, $CD4^+$ T-cells are known in the art to play a critical role in T1D pathology (Anderson, et al., 2005, *Annual review of immunology* 23: 447-85). Prior to diagnosis of T1D, pancreatic islets are infiltrated by inflammatory cells including $CD4^+$ T-cells and antibodies to various β-cell antigens. These proteins are present in the sera of patients at risk (Kent et al., 2005, *Nature* 435: 224-8; Achenbach et al., 2005, *Current diabetes reports* 5:98-103).

It has been suggested that autoimmune destruction of β-cells and diabetes onset may be associated with a reduction in regulatory T-cell (Treg) numbers and/or functions (Waid et al., 2008, *Journal of leukocyte biology* 84:431-9; Brode et al., 2006, *Journal of immunology* 177:6603-12). On the other hand, antigen presenting cells (APCs) in NOD mice and T1D patients have been shown to be defective in their ability to stimulate $CD4^+CD25^+$ Treg function although the Tregs themselves appear to be functional (Alard et al., 2006, *Diabetes* 55:2098-105; Manirarora et al., 2008, *PloS one* 3: e3739). The inventors and others in the art have shown that restoring Treg function or inducing adaptive Tregs may be an effective method for preventing and or stabilizing autoimmune diabetes (Cheatem et al., 2009, *Clin Immunol* 131: 260-70; Gaudreau et al., 2007, *J. Immunol.* 179: 3638-47; Karumuthil-Melethil et al., 2010, *Journal of immunology* 184:6695-708; You et al., 2007, *Proceedings of the National Academy of Sciences of the United States of America* 104: 6335-40).

Existing and emerging therapies in the art utilize broad-based immunoregulatory strategies, such as inhibition or deletion of lymphocytes subsets and/or establishing immune tolerance via activation of Tregs and include for example non-mitogenic anti-CD3 or anti-thymocyte globulin (Chatenoud 2003, *Nature reviews. Immunology* 3: 123-32; Chung et al., 2007, *International immunology* 19: 1003-10). These approaches, however, result in global attenuation of the immune response and render the patient susceptible to opportunistic infections and cancers. In this regard, biologics including monoclonal antibodies (mAbs) and tumor necrosis factor (TNF) inhibitors are commonly prescribed to individuals suffering from autoimmune diseases (O'Shea et al., 2002, *Nature reviews. Immunology* 2:37-45). Three licensed mAbs (adalimumab, etanercept and infliximab) are currently on the market for the treatment of immune mediated inflammatory diseases, including diabetes mellitus (Silva et al., 2010, *Immunotherapy* 2: 817-33). However, in September 2008, the FDA announced that manufacturers of TNF inhibitors must strengthen existing warnings on the risk of fungal infections, in particular, histoplasmosis.

As a result, safer, targeted therapeutics are needed in the art. A highly desired alternative approach is the induction of T-cell tolerance to β-cell antigens for prevention of disease development in patients at risk or with recent onset of disease. Central to the immune response are T-cells whose activity can be up- or down-regulated resulting in an immune response that attacks or ignores an antigen, respectively. The ability to down-regulate or become tolerant to specific antigens is crucial for preventing or treating autoimmune diseases. Current clinical approaches for these indications are not target specific and result in global attenuation of the immune response, however. It is therefore beneficial to selectively suppress self-reactive T-cells while leaving the rest of the immune system intact. To do so, T-cell expressed cell surface markers provide a convenient and specific target for inducing desired immunomodulation.

Cytotoxic T-Lymphocyte Antigen 4 (CTLA-4) is a cell surface marker molecule expressed on activated T-cells that plays a critical role in maintaining peripheral tolerance and has been linked to insulin-dependent diabetes (IDD) disease susceptibility in both human patients and NOD mice (Todd et al., 2001, *Immunity* 15: 387-95; Karumuthil-Melethil et al., Id.; Tivol et al., 1995, *Immunity* 3: 541-7). It has been demonstrated that peripheral T-cell tolerance in vivo requires CTLA-4 engagement (Shrikant et al., 1999, *Immunity* 11: 483-93; Ratts et al., 1999, *Int Immunol* 11: 1889-96; Schwarz et al., 2000, *J Immunol* 165: 1824-31; Chai et al., 2000, *J Immunol* 165: 3037-42). T-cell activation requires T-cell receptor engagement of its cognate antigen-MHC complex and CD28 binding to the B7 ligands (i.e. CD80 and CD86) on APCs. Activation of T-cells results in increased expression of the T-cell surface molecule CTLA-4 (Bluestone, 1997, *J Immunol* 158: 1989-93; Linsley et al., 1994, *Immunity* 1: 793-801). Use of CTLA-4-Ig which blocks co-stimulation has been widely explored for treating autoimmunity and transplant rejection (Londrigan et al., 2010, *Transplantation* 90: 951-7; Vergani et al., 2010, *Diabetes* 59: 2253-64). However, this approach down-modulates all activated T-cells and can cause generalized immune suppression. Therefore, this exploration has not been very successful. Because signaling through CTLA-4 down modulates T-cell responses, engagement of CTLA-4 in a targeted fashion has been explored for treating several experimental autoimmune diseases (Karumuthil-Melethil et al., Id.; Fife et al., 2006, *The Journal of clinical investigation* 116: 2252-61; Li et al., 2007, *J Immunol* 179: 5191-203; Vasu et al., 2003, *Int Immunol* 15: 641-54).

Although various pancreatic β-cell specific antigens have been described in the art, none of them is expressed on the cell surface plasma membranes. GLUT2 is a molecule that is expressed on pancreatic β-cell surfaces predominantly (although not completely) where it forms a part of "the glucose sensor" (Thorens et al., 1994, *Biochem Soc Trans* 22: 684-7). Encoded by the SLC2A2 gene in mammals, GLUT2 is a 524 amino acid multi-pass transmembrane carrier protein. Id. The longest stretch of extracellular domain is 67 amino acids long (UniProtKB/Swiss-Prot entry P11168). GLUT2 is involved in passive glucose transport while not being directly involved in disease pathogenesis and thus is an available target for specific binding to, inter alia, an antibody.

SUMMARY OF THE INVENTION

This invention as disclosed provides reagents and methods for treating and preventing Type 1 diabetes in an animal, particularly a human. The reagents of the invention comprise proteins that specifically bind to GLUT2 protein expressed on the cell surface of a pancreatic β-cell and CTLA-4 expressed on the cell surface of an activated T-cell. As set forth in greater detail herein, binding of the protein to both the GLUT2 and CTLA-4 induces Treg cells that down-regulate the autoimmune responses to pancreatic β-cells that are involved in the development of Type 1 diabetes. In addition, the method disclosed herein can be used to treat human T1D via use of a recombinant ScFv BsAb with the properties as described above, Upon in vivo delivery, this recombinant ScFv-BsAb is will accumulate on β-cell surface in the pancreatic tissue and the CTLA-4 specific arm will cross-link CTLA-4 on activated T-cells infiltrating the target tissue and initiate inhibitory signal in them. Such a therapy is expected to modulate β-cell specific T cell responses and suppress T1D.

In one embodiment, the invention as disclosed herein is a protein comprising a first polypeptide or polypeptide domain having a first specific binding activity for Cytotoxic T-lymphocyte Antigen 4 (CTLA-4) expressed on a T-cell cell surface and a second specific binding activity for Glucose Transporter 2 (GLUT2) or an extracellular ectodomain thereof expressed on a pancreatic β-cell cell surface, wherein binding of the first polypeptide or polypeptide domain to CTLA-4 induces a CTLA-4 specific agonist response in the T cell, and binding of the second polypeptide or polypeptide domain to GLUT2 or an ectodomain thereof does not inhibit GLUT2 glucose transporter function, wherein said agonist response in the T cell induces a response that reduces immunoreactivity against pancreatic β-cells. In certain embodiments, the invention as disclosed has a first and second polypeptide or polypeptide domain that are independently an antibody molecule or a specific-binding fragment thereof, and may further have a first and second polypeptide or polypeptide domain independently comprising at least one immunoglobulin heavy chain and one immunoglobulin light chain. In additional embodiments, the first and second polypeptide or polypeptide domain independently comprise a monovalent antibody fragment, an F(ab) fragment, an F(ab)2 fragment, F(ab)' fragment, or an Fv fragment. The invention as disclosed herein may also have the first and second polypeptide or polypeptide domains covalently attached to one another by a linker moiety.

In another embodiment, the invention as disclosed herein is a pharmaceutical composition comprising the protein described above with a pharmaceutically acceptable carrier or adjuvant. In a certain embodiments, the pharmaceutical composition is used in methods for preventing diabetes in an animal comprising the step of administering to the animal a therapeutically effective amount of a pharmaceutical composition of the invention. In further embodiments, the methods are used for protecting pancreatic β-cells in an animal by administering to the animal a protective amount of the pharmaceutical composition.

In one embodiment, the invention as disclosed herein comprises methods for producing Treg cells that down-regulate autoimmune responses to pancreatic β-cells in an animal comprising the step of administering to the animal an effective amount of a pharmaceutical composition disclosed herein. In certain embodiments of the methods, the pancreatic tissue-specific T cells are down modulated and induced Treg cells are predominantly pancreatic tissue-specific Treg cells.

In another embodiment, the invention as disclosed herein provides methods for producing immune tolerance to pancreatic β-cells in an animal comprising the step of administering to the animal an effective amount of a pharmaceutical composition as set forth herein. In certain embodiments of the methods, immune tolerance is pancreatic islet β-cell specific T cell tolerance. In one embodiment, the invention as disclosed herein provides a protein comprising a first polypeptide or polypeptide domain having a first specific binding activity for Cytotoxic T-lymphocyte Antigen 4 (CTLA-4) expressed on a T-cell cell surface and a second specific binding activity for Glucose Transporter 2 (GLUT2) or an extracellular ectodomain thereof expressed on a pancreatic beta-cell surface, wherein binding of the first polypeptide or polypeptide domain to CTLA-4 induces a CTLA-4 specific agonist response in the T cell, and binding of the second polypeptide or polypeptide domain to GLUT2 or an ectodomain thereof does not inhibit GLUT2 glucose transporter function, wherein said agonist response in the T cell reduces immunoreactivity against pancreatic beta cells.

In another embodiment, the invention as disclosed herein provides a pharmaceutical composition comprising the protein as disclosed herein with a pharmaceutically acceptable carrier or adjuvant.

In another embodiment, the invention as disclosed herein provides a method for preventing diabetes in an animal comprising the step of administering to the animal a therapeutically effective amount of the pharmaceutical composition as disclosed herein.

In another embodiment, the invention as disclosed herein provides a method for protecting pancreatic β-cells in an animal comprising the step of administering to the animal a protective amount of the pharmaceutical composition as disclosed herein.

In another embodiment, the invention as disclosed herein provides a method of producing Treg cells that down-regulate autoimmune responses to pancreatic β-cells in an animal comprising the step of administering to the animal an effective amount of the pharmaceutical composition as disclosed herein.

In another embodiment, the invention as disclosed herein provides a method of producing immune tolerance to pancreatic β-cells in an animal comprising the step of administering to the animal an effective amount of the pharmaceutical composition as disclosed herein.

Additional features and advantages are described herein, and will be apparent from the following Detailed Description, Drawings and the claims.

DETAILED DESCRIPTION

Figure 1:
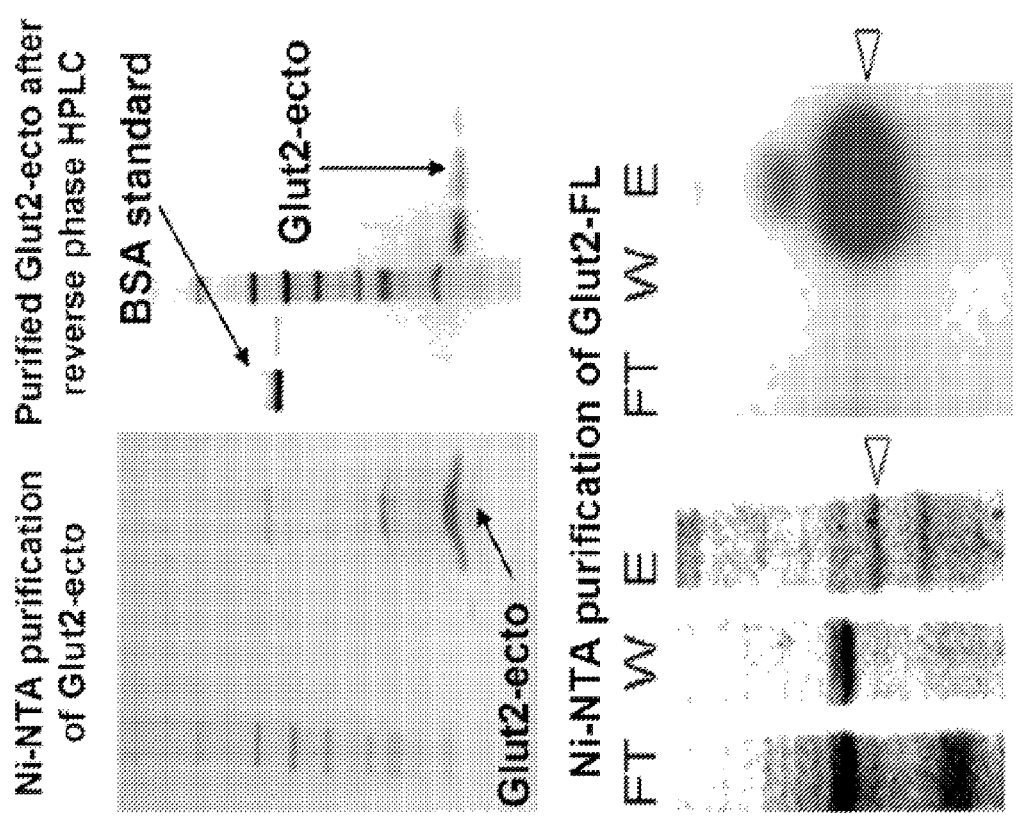
FIG. 1 shows nickel nitriloacetic acid (Ni-NTA) affinity and reverse phase HPLC purification of recombinant ecto-GLUT2 from E. coli lysate (upper panels) and Ni-NTA purification of recombinant full-length GLUT2 from HEK-293 cell lysate (lower panels).

Provided herein are reagents and methods for treating or preventing Type 1 (insulin-dependent) diabetes (T1D) in a mammal, most particularly a human. The invention provides proteins made up of two different specific binding domains, including in certain embodiments monoclonal antibodies or specific-binding fragments thereof, wherein one specific-binding domain binds to Glucose transporter 2 (GLUT2) expressed predominantly on pancreatic β-cells, while the other specific binding domain binds to Cytotoxic T-Lymphocyte Antigen 4 (CTLA-4), a cell surface molecule on activated T-cells. Also provided are pharmaceutical compositions of the disclosed proteins and methods for using said pharmaceutical compositions for administration to mammals, particularly humans, for therapy or prophylaxis of T1D.

Without being bound to any particular description regarding mechanism of action, it is envisioned that, upon binding to pancreatic β-cells with the targeting (GLUT2-specific) arm, the anti-CTLA-4 arm is available to bind to activated antigen-specific T-cells that localize to the pancreatic islets. Binding of a protein of the invention can suppress effector (pathogenic) T-cell function, thereby inducing Tregs in a β-cell antigen-specific manner and overcoming the limitations of generalized immunosuppressants that have been used for treating other diseases and disorders having an autoimmunity component. Earlier studies by the inventors have shown that concurrent enhanced engagement of T-cell receptor and CTLA-4 on activated T-cells leads to induction of antigen-specific Tregs (Karumuthil-Melethil et al., Id.; Li et al., 2007, *J Immunol* 179: 5191-203; Vasu et al., 2003, *Int Immunol* 15: 641-54). As disclosed herein, anti-GLUT2/anti-CTLA-4 proteins of the invention can bind simultaneously to GLUT2 expressed on β-cells and engage CTLA-4 expressed on islet-infiltrating T-cells, resulting in down-modulation of β-cell specific T-cell responses, thereby inducing Tregs that can suppress autoimmunity in T1D.

CTLA-4 engagement down-regulates T-cell responses through different mechanisms including induction of IL-10 and TGF-β (Karumuthil-Melethil et al., Id.). Therefore, targeted engagement of CTLA-4 on activated T-cells can be used to generate antigen/tissue specific Tregs for, inter alia, the treatment of diabetes. Disclosed herein is a novel approach to engage CTLA-4 on islets-infiltrating T-cells by, in certain embodiments, β-cell surface bound CTLA-4 specific agonistic antibodies. Since GLUT2 is predominantly found on pancreatic β-cells, this marker is capable of selectively anchoring to pancreatic β-cells molecules that specifically bind to CTLA-4, in certain embodiments being anti-CTLA-4 antibodies, onto the pancreatic β-cell surface. It is understood in the art that most activated autoreactive T-cells in T1D reside in the pancreatic microenvironment. Therefore, pancreatic islet specific T-cell tolerance can be induced by administration of a protein of the invention. Advantageously, minimal and transient non-tissue specific protein binding and related side effects are produced because CTLA-4 is expressed at a very low level on resting T-cells. In addition, any such binding would be, in most instances, remote from any ongoing T-cell receptor engagement and would not inhibit normal immune surveillance. Hence, the methods disclosed herein provide an advantageous alternative to current experimental therapies that lack specificity (such as anti-CD3, anti-CD20, etc.).

The section headings are used herein for organizational purposes only, and are not to be construed as in any way limiting the subject matter described. The invention as disclosed herein is not limited to the particular methodology, protocols, cell lines, vectors, or reagents described herein because they may vary without departing from the spirit and scope of the invention.

Conventional and standard techniques may be used for recombinant DNA molecule, protein, and antibody production, as well as for tissue culture and cell transformation. Enzymatic reactions and purification techniques are typically performed according to the manufacturer's specifications or as commonly accomplished in the art using conventional procedures known in the art, or as described herein. Unless specific definitions are provided, the nomenclature utilized in connection with, and the laboratory procedures and techniques of analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients.

Further, the terminology used herein is for the purpose of exemplifying particular embodiments only and is not intended to limit the scope of the invention as disclosed herein. Any method and material similar or equivalent to those described herein can be used in the practice of the invention as disclosed herein and only exemplary methods, devices, and materials are described herein.

All patents and publications mentioned herein are incorporated by reference in their entirety for the purpose of describing and disclosing the proteins, enzymes, vectors, host T-cells, and methodologies reported therein that might be used with and in the invention as disclosed herein. However,

1. DEFINITIONS

As utilized in accordance with the present disclosure, the following terms unless otherwise indicated, shall be understood to have the following meanings:

The term "antibody" is used in the broadest sense, and specifically covers monoclonal antibodies (including full-length monoclonal antibodies), polyclonal antibodies, antibody fragments, or synthetic polypeptides carrying one or more CDR or CDR-derived sequences so long as the polypeptides exhibit the desired biological activity. Antibodies (Abs) and immunoglobulins (Igs) are glycoproteins having the same structural characteristics. Generally, antibodies are considered Igs with a defined or recognized specificity. Thus, while antibodies exhibit binding specificity to a specific target, immunoglobulins include both antibodies and other antibody-like molecules that lack target specificity. The antibodies of the invention can be of any class (e.g., IgG, IgE, IgM, IgD, IgA and so on), or subclass (e.g., $IgG_1$, $IgG_2$, $IgG_{2a}$, $IgG_3$, $IgG_4$, $IgA_1$, $IgA_2$ and so on) ("type" and "class," and "subtype" and "subclass," are used interchangeably herein). Native or wildtype (obtained from a non-artificially manipulated member of a population) antibodies and immunoglobulins are usually heterotetrameric glycoproteins of about 150,000 daltons, composed of two identical light (L) chains and two identical heavy (H) chains. Each heavy chain has at one end a variable domain ($V_H$) followed by a number of constant domains. Each light chain has a variable domain at one end ($V_L$) and a constant domain at the other end. The term "non-artificially manipulated" means not treated to contain or express a foreign antigen-binding molecule. Wildtype can refer to the most prevalent allele or species found in a population or to the antibody obtained from a non-manipulated animal, as compared to an allele or polymorphism, or a variant or derivative obtained by a form of manipulation, such as mutagenesis, use of recombinant methods and so on to change an amino acid of the antigen-binding molecule.

As used herein, "anti-CTLA-4 antibody" means an antibody or polypeptide derived therefrom (a derivative) that binds specifically to CTLA-4 as defined herein, including, but not limited to, molecules which inhibit or substantially reduce the binding of CTLA-4 to its receptor or inhibit CTLA-4 activity.

As used herein, "anti-GLUT2 antibody" means an antibody or polypeptide derived therefrom (a derivative) that binds specifically to GLUT2 as defined herein. In certain embodiments, the term includes molecules that do not inhibit or substantially GLUT2 activity.

As used herein, in certain embodiments "protein" means a first polypeptide or polypeptide domain having a first specific binding activity for Cytotoxic T-lymphocyte Antigen 4 (CTLA-4) expressed on a T-cell cell surface and a second specific binding activity for Glucose Transporter 2 (GLUT2) or an extracellular ectodomain thereof expressed on a pancreatic β-cell cell surface.

"Agonist" or "agonist activity" refers to the ability of an anti-CTLA-4 antibody to induce signaling through CTLA-4 expressed on activated T cells that results in down modulation of T-cell response, and induction of T-reg cells that can down-modulate or suppress the activity of other effector T-cells.

"Antagonist" refers to a molecule capable of inhibiting one or more biological activities of a target molecule, such as signaling by CTLA-4. Antagonists may interfere with the binding of a receptor to a ligand and vice versa, by incapacitating or killing cells activated by a ligand, and/or by interfering with receptor or ligand activation (e.g., tyrosine kinase activation) or signal transduction after ligand binding to a receptor. The antagonist may completely block receptor-ligand interactions or may substantially reduce such interactions.

The term "antigen" as used herein refers to a molecule or a portion of a molecule capable of being bound by the antibodies of the invention. An antigen can have one or more than one epitope.

The term "antigen binding domain," "antigen binding site," or "antigen binding region" refers to that portion of a protein molecule, in particular an antibody, which contains the specific amino acid residues (or other moieties) that interact with an antigen and confer on the binding agent its specificity and affinity for the antigen. In an antibody, the antigen-binding domain is commonly referred to as the "complementarity-determining region" (or "CDR"). Where an antigen is large, an antibody may only bind to a particular part of the antigen, which part is called an epitope. An antigen-binding domain may be provided by one or more antibody variable domains. In certain aspects, an antigen-binding domain is made of the association of an antibody light chain variable domain ($V_L$) and an antibody heavy chain variable domain ($V_H$).

The term "epitope" refers to that portion of any molecule capable of being recognized by and bound by an antibody, at one or more of the binding agent's antigen binding regions. Epitopes usually consist of chemically active surface groupings of molecules, such as for example, amino acids or carbohydrate side chains, and have specific three-dimensional structural characteristics as well as specific charge characteristics. Epitopes as used herein may be contiguous or non-contiguous. Moreover, epitopes may be mimetic in that they comprise a three-dimensional structure that is identical to the epitope used to generate the antibody, yet comprise none or only some of the amino acid residues found in the antigen molecule (in particular, CTLA-4 or GLUT2) used to stimulate the antibody immune response.

The term "antibody fragment" refers to a portion of an intact or a full-length chain or an antibody, generally comprising a target binding or variable region. Examples of antibody fragments include, but are not limited to, Fab, Fab', $F(ab')_2$ and Fv fragments. A "functional fragment" or "analog of an anti-CTLA-4/GLUT2 antibody" is one that can prevent or substantially reduce the ability of the receptor to bind to a ligand or to initiate signaling. As used herein, the term "functional fragment" generally is synonymous with "antibody fragment," and with respect to antibodies, can refer to fragments such as Fv, Fab, $F(ab')_2$, and so on which can prevent or substantially reduce the ability of the receptor to bind to a ligand or to initiate signaling. An "Fv" fragment consists of a dimer of one heavy and one light chain variable domain in a non-covalent association ($V_H$-$V_L$ dimer). In that configuration, the three CDRs of each variable domain interact to define a target binding site on the surface of the $V_H$-$V_L$ dimer, as in an intact antibody. Collectively, the six CDRs confer target binding specificity on the intact antibody. However, even a single variable domain (or half of an Fv comprising only three CDRs specific for a target) can have the ability to recognize and to bind target. The Fab fragment contains the variable and constant domains of the light chain and the variable and first constant domain ($C_{H1}$) of the heavy chain. Fab' fragments differ from Fab fragments by the addition of a few residues at the carboxyl terminus of the $C_{H1}$ domain to include one or more cysteines from the antibody hinge region. Fab' fragments can be produced by cleavage of the disulfide bond at the hinge cysteines of the F(ab')$_2$ pepsin digestion product. Additional enzymatic and chemical treatments of antibodies can yield other functional fragments of interest.

The term "autoimmune disease" as used herein refers to a non-malignant disease or disorder arising from and directed against an individual's own tissues. In certain embodiments, the autoimmune disease or disorder of the invention includes, but is not limited to, diabetes mellitus, specifically Type I diabetes mellitus or insulin dependent diabetes mellitus.

The term, "carrier" refers to a diluent, adjuvant, excipient or vehicle with which the therapeutic is administered. Such physiological carriers can be sterile liquids, such as water and oils, including those of petroleum, animal, vegetable or synthetic origin, such as peanut oil, soybean oil, mineral oil, sesame oil and the like. Water is a suitable carrier when the pharmaceutical composition is administered intravenously. Saline solutions and aqueous dextrose and glycerol solutions also can be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The composition, if desired, can also contain minor amounts of wetting or emulsifying agents, or pH buffering agents. The compositions can take the form of solutions, suspensions, emulsions, tablets, pills, capsules, powders, sustained-release formulations, depots, and the like. Such compositions will contain an effective amount of the antibody, preferably in purified form, together with a suitable amount of carrier so as to provide the form for proper administration to the patient. As known in the art, specific formulations are constructed to suit the mode of administration.

The terms "cell," "cell line," and "cell culture" include progeny thereof. It is also understood that all progeny may not be precisely identical, such as in DNA content, due to deliberate or inadvertent mutation. Variant progeny that have the same function or biological property of interest, as screened for in the original cell, are included.

The term "CDR grafted antibody" refers to an antibody in which the CDR from one antibody of a particular species or isotype is recombinantly inserted into the framework of another antibody of the same or different species or isotype.

"Derivatives" include those proteins and particularly antibodies that have been chemically modified in some manner distinct from insertion, deletion, or substitution variants.

As used herein, the terms "effective amount" and "therapeutically effective amount" refer to the amount of a therapy (e.g., a prophylactic or therapeutic agent), which is sufficient to reduce the severity and/or duration of T1D, ameliorate one or more symptoms thereof, prevent the advancement of T1D or cause regression of T1D, or which is sufficient to result in the prevention of the development, recurrence, onset, or progression of T1D or one or more symptoms thereof, or enhance or improve the prophylactic and/or therapeutic effects of another therapy (e.g., another therapeutic agent) useful for treating T1D.

The term "expression vector" refers to a plasmid, phage, virus, or other recombinant genetic vector, for expressing a polypeptide from a DNA (or in some instances an RNA) molecule. An expression vector can comprise a transcriptional unit comprising an assembly of (1) a genetic element or elements having a regulatory role in gene expression, for example, promoters, or enhancers, (2) a structural genetic component or sequence that encodes the binding agent which is transcribed into mRNA and translated into protein, and (3) appropriate transcription initiation and termination sequences. Structural genetic components intended for use in yeast or eukaryotic expression systems preferably include a leader sequence enabling extracellular secretion of translated protein by a host T-cell. Alternatively, where a recombinant antibody is expressed without a leader or transport sequence, it may include an amino terminal methionine residue. This residue may or may not be subsequently cleaved from the expressed recombinant protein to provide a final antibody product.

Also included within the scope of the invention are functional equivalents of antibody-comprising embodiments of the proteins disclosed herein. The term "functional equivalents" includes antibodies with homologous sequences, antibody homologs, chimeric antibodies, artificial antibodies and modified antibodies, for example, wherein each functional equivalent is defined by the ability to bind to CTLA-4 and/or GLUT2, inhibiting CTLA-4 signaling ability or function, or inhibiting binding of CTLA-4 to its receptor. The skilled artisan will understand that there is an overlap in the group of molecules termed "antibody fragments" and the group termed "functional equivalents." Methods of producing functional equivalents that retain CTLA-4 binding ability are known to the person skilled in the art.

The terms "functional fragment," "variant," "derivative," "analog," and the like, as well as forms thereof, of an antibody or antigen refer to a compound or molecule having qualitative biological activity in common with a full-length antibody or antigen of interest. For example, a functional fragment or analog of an anti-CTLA-4 and/or GLUT2 antibody is one that can bind to a CTLA-4 and/or GLUT2 molecule or one that can prevent or substantially reduce the ability of a ligand, or an agonistic or antagonistic antibody, to bind to CTLA-4 and/or GLUT2.

The term "heavy chain" when used in reference to an antibody collectively refers to five distinct types, called alpha, delta, epsilon, gamma, and mu, based on the amino acid sequence of the heavy chain constant domain. The combination of heavy and light chains give rise to five known classes of antibodies: IgA, IgD, IgE, IgG, and IgM, respectively, including four known subclasses of IgG, designated as IgG$_1$, IgG$_2$, IgG$_3$, and IgG$_4$.

As used herein, the term "humanization" is related to used of the mouse humoral immune system. Introduction of human immunoglobulin (Ig) loci into mice in which the endogenous Ig genes have been inactivated offers the opportunity to study mechanisms underlying programmed expression and assembly of antibodies as well as their role in B-cell development. Furthermore, such a strategy provides a source for production of fully human monoclonal antibodies (MAbs).

The term "human antibody" includes antibodies having variable and constant regions substantially corresponding to human germline immunoglobulin sequences. In certain embodiments, human antibodies are produced in non-human mammals, including, but not limited to, rodents, such as mice and rats, and lagomorphs, such as rabbits. In certain embodiments, human antibodies are produced in hybridoma cells. In certain embodiments, human antibodies are produced recombinantly.

The term "hinge" or "hinge region" as used herein refers to the flexible polypeptide comprising the amino acids between the first and second constant domains of an antibody.

"Antibody homolog" or "homolog" refers to any molecule which specifically binds to a particular antigen as taught herein and in particular CTLA-4 or GLUT2. Thus, an antibody homolog includes native or recombinant antibodies, whether modified or not, portions of antibodies (such as an Fab or Fv molecule) that retain the biological properties of interest, such as binding to CTLA-4 or GLUT2, a single chain antibody, a polypeptide carrying one or more CDR regions and so on. The amino acid sequence of the homolog need not be identical to that of the naturally occurring antibody but can be altered or modified to carry substitute amino acids, inserted amino acids, deleted amino acids, amino acids other than the twenty normally found in proteins, and so on to obtain a polypeptide with enhanced or other beneficial properties.

The terms "identity" or "homology" refer to the percentage of nucleotide bases or amino acid residues in the candidate sequence that are identical with the residue of a corresponding sequence to which it is compared after aligning the sequences and introducing gaps, if necessary, to achieve the maximum percent identity for the entire sequence, and not considering any conservative substitutions as part of the sequence identity. Neither N-terminal or C-terminal extensions nor insertions shall be construed as reducing identity or homology. Methods and computer programs for the alignment are available and well known in the art. Sequence identity may be measured using sequence analysis software.

The term "inhibiting and/or neutralizing epitope" is an epitope which when bound by an antibody, results in the loss of (or at least the decrease in) biological activity of the molecule, cell, or organism containing such epitope, in vivo, in vitro, or in situ. In the context of the invention disclosed herein, the neutralizing epitope is located on or is associated with a biologically active region of CTLA-4 or GLUT2. Alternatively, the term "activating epitope" is an epitope, which when bound by an antibody of the invention, such as an antibody, results in activation, or at least maintenance of a biologically active conformation, of CTLA-4 or GLUT2.

The term "isolated" when used in relation to proteins and particular antibodies of the invention refers to a compound that is free from at least one contaminating polypeptide or compound that is found in its natural environment, and preferably substantially free from any other contaminating mammalian polypeptides that would interfere with its therapeutic or diagnostic use.

An "isolated" or "purified" protein and particular an antibody is substantially free of cellular material or other contaminating proteins from the cell or tissue source or medium from which the protein is derived, or substantially free of chemical precursors or other chemicals when chemically synthesized. Generally, "purified" will refer to a protein and particular an antibody composition that has been subjected to fractionation to remove various other components, and which composition substantially retains its expressed biological activity. The language "substantially free of cellular material" includes preparations of a protein and particular an antibody in which the polypeptide is separated from cellular components of the cells from which a protein and particular an antibody is isolated or recombinantly produced. Thus, a protein and particular an antibody that is substantially free of cellular material includes preparations of the protein and particular antibody having less than about 30%, 20%, 10%, 5%, 2.5%, or 1% (by dry weight) of contaminating protein. Where the term "substantially purified" is used, this designation will refer to an antibody composition in which the protein and particular antibody forms the major component of the composition, such as constituting about 50%, about 60%, about 70%, about 80%, about 90%, about 95%, or more of the proteins in the composition.

When the protein and particular an antibody is recombinantly produced, it is also preferably substantially free of culture medium, i.e., culture medium represents less than about 20%, 10%, 5%, 2.5%, or 1% of the volume of the protein preparation. When a protein and particular an antibody is produced by chemical synthesis, it is preferably substantially free of chemical precursors or other chemicals and reagents, i.e., the protein and particular antibody of interest is separated from chemical precursors or other chemicals that are involved in the synthesis of the protein. Accordingly, such preparations of the protein and particular antibody have less than about 30%, 20%, 10%, 5%, or 1% (by dry weight) of chemical precursors or compounds other than antibody of interest. In a preferred embodiment of the invention, proteins and particularly antibodies are isolated or purified.

The proteins and particular antibodies of interest can be screened or can be used in an assay as described herein or as known in the art. Often, such assays require a reagent to be detectable, which is, for example, labeled. The word "label" when used herein refers to a detectable compound or composition that can be conjugated directly or indirectly to a molecule or protein, e.g., an antibody. The label may itself be detectable (e.g., radioisotope labels, particles, or fluorescent labels) or, in the case of an enzymatic label, may catalyze chemical alteration of a substrate compound or composition that is detectable.

The term "light chain" when used in reference to an antibody collectively refers to two distinct types, called kappa (k) or lambda (l) based on the amino acid sequence of the constant domains.

The term "linear Fab" refers to a tetravalent antibody. The "linear Fab" is composed of a tandem of the same $C_{H1}$-$V_H$ domain, paired with the identical light chain at each $C_{H1}$-$V_H$ position.

The term "linker" as used herein refers to a molecule and particularly a peptide adapted to connect the variable domains of the protein and particularly antibody constructs of the invention. A peptide linker may contain one or a plurality of any amino acids, the amino acids glycine (G) and serine (S) being preferred. The linkers may be equal or differ from each other between and, when used with antibodies within the heavy chain polypeptide and the light chain polypeptide. Furthermore, the linker may have a length of 1, 2, 3, 4, 5, 6, 7, 8, 9, 10, 11, 12, 13, 14, 15, 16, 17, 18, 19, or 20 amino acids. A preferred peptide linker unit for antibody heavy chain and light chain domains is GGGGS (SEQ ID NO.: 1). The numbers of linker units of the heavy chain and of the light chain may be equal (symmetrical order) or differ from each other (asymmetrical order). A peptide linker is preferably long enough to provide an adequate degree of flexibility to prevent the protein and particularly antibody moieties from interfering with each other's activity, for example by steric hindrance, to allow for proper protein folding and, if necessary, to allow the molecules to interact with two or more, possibly widely spaced, receptors on the same cell; yet it is preferably short enough to allow moieties such as the antibody moieties to remain stable in the cell.

As used herein, the phrase "low to undetectable levels of aggregation" refers to samples containing no more than 5%, no more than 4%, no more than 3%, no more than 2%, no more than 1%, and often no more than 0.5% aggregation, by weight protein, as measured by, for example, high performance size exclusion chromatography (HPSEC).

As used herein, the term "low to undetectable levels of fragmentation" refers to samples containing equal to or more than 80%, 85%, 90%, 95%, 98%, or 99%, of the total protein, for example, in a single peak, as determined by HPSEC, or in two (2) peaks (heavy chain and light chain) as determined by, for example, reduced capillary gel electrophoresis (rCGE), and containing no other single peaks having more than 5%, more than 4%, more than 3%, more than 2%, more than 1%, or more than 0.5% of the total protein, each. rCGE as used herein refers to capillary gel electrophoresis under reducing conditions sufficient to reduce disulfide bonds in an antibody or antibody-type or derived molecule.

"Animal" for purposes of treatment refers to any animal classified as a mammal, including humans, domestic and farm animals, non-human primates, and zoo, sports or pet animals, such as dogs, horses, cats, and cows. In particular, NOD mice represent a well-established mouse model of T1D that resembles many features of human T1D including lymphocytic infiltration into pancreatic tissue with eventual β-cell destruction resulting in hyperglycemia, abrupt onset of overt diabetes, ketosis proneness, absence of obesity and the dependence on exogenous insulin to sustain life (Todd and Wicker, 2001, *Immunity* 15: 387-95; Tang et al., 2006, *Nature immunology* 7: 83-92; Trembleau et al., 1995, *The Journal of experimental medicine*, 181: 817-21). Certain evidence known in the art suggests that regulatory T (Treg) cells control the progression of diabetes (Chen et al., 2005, *J Exp Med* 202: 1387-97.

The term "monoclonal antibodies" refers to a collection of antibodies encoded by the same nucleic acid molecule(s), which are optionally produced by a single hybridoma or other cell line or by a transgenic mammal such that each monoclonal antibody will typically recognize the same epitope on the antigen. The term "monoclonal" is not limited to any particular method for making the antibody, nor is the term limited to antibodies produced in a particular species, e.g., mouse and rat. Monoclonal antibodies are highly specific, being directed against a single target site, epitope, or determinant. Furthermore, in contrast to conventional (polyclonal) antibody preparations that typically include different antibodies directed against different determinants (epitopes) of an antigen, each monoclonal antibody is directed against a single determinant on the target. In addition to their specificity, monoclonal antibodies are advantageous by being synthesized by a host cell, uncontaminated by other immunoglobulins, which provides for cloning the relevant gene and mRNA encoding the antibody chains thereof. The modifier "monoclonal" indicates the character of the antibody as being obtained from a substantially homogeneous population of antibodies, and is not to be construed as requiring production of the antibody by any particular method. For example, the monoclonal antibodies for use with the invention as disclosed herein may be isolated from phage antibody libraries using well-known techniques or can be purified from a polyclonal preparation, as well as by conventional hybridoma technologies. The parent monoclonal antibodies to be used in accordance with the invention may be made by classic hybridoma methods or may be made by recombinant techniques.

The term "naturally occurring" when used in connection with biological materials such as nucleic acid molecules, proteins and polypeptides, host cells, and the like, refers to those which are found in nature and not modified by a human being.

The term "pharmaceutical composition" as used herein refers to formulations of various preparations for administration to an animal, particularly a human. The formulations containing therapeutically effective amounts of the proteins, particularly antibodies of the invention are sterile liquid solutions, liquid suspensions, or lyophilized versions, and optionally contain stabilizers or excipients.

Proteins of the invention, including certain embodiments comprising antibodies or antigen-binding fragments thereof, may be provided in pharmaceutically acceptable compositions as known in the art or as described herein. The term "physiologically acceptable," "pharmacologically acceptable," and so on mean approved by a regulatory agency of the Federal or a state government or listed in the U.S. Pharmacopeia or other generally recognized pharmacopeia for use in animals and more particularly in humans.

"Single-chain Fv," "sFv," or "scAb" antibody fragments comprise the $V_H$ and $V_L$ domains of an antibody, wherein these domains are present in a single polypeptide chain. Generally, the Fv polypeptide further comprises a polypeptide linker, often a flexible molecule, between the $V_H$ and $V_L$ domains, which enables the sFv to form the desired structure for target binding.

"Specifically binds CTLA-4" or "specifically binds GLUT2" refers to the ability of a specific binding agent (such as an antibody or fragment thereof) of the invention to recognize and bind mature, full-length or partial-length mouse CTLA-4 or GLUT2 polypeptide, or an ortholog thereof, such that its affinity (as determined by, e.g., affinity ELISA or BIAcore assays as described herein) or its neutralization capability (as determined by, e.g., neutralization ELISA assays described herein, or similar assays) is at least 10 times as great, but optionally 50 times as great, 100, 250, or 500 times as great, or even at least 1000 times as great as the affinity or neutralization capability of the same for any other interleukin or other peptide or polypeptide.

The phrase "substantially identical" with respect to an antibody chain polypeptide sequence may be construed as an antibody chain exhibiting at least 70%, 80%, 85%, 90%, 91%, 92%, 93%, 94%, 95%, 96%, 97%, 98%, 99%, or more sequence identity to the reference polypeptide sequence. The term with respect to a nucleic acid sequence may be construed as a sequence of nucleotides exhibiting at least about 85%, 90%, 91%, 92%, 93%, 94%, 95%, 96%, 97%, 98%, 99%, or more sequence identity to the reference nucleic acid sequence.

"Substitutional" variants are those that have at least one amino acid residue in a native sequence removed and replaced with a different amino acid inserted in its place at the same position. The substitutions may be single, where only one amino acid in the molecule is substituted, or may be multiple, where two or more amino acids are substituted in the same molecule. The plural substitutions may be at consecutive sites. Also, one amino acid can be replaced with plural residues, in which case such a variant comprises both a substitution and an insertion. "Insertional" variants are those with one or more amino acids inserted immediately adjacent to an amino acid at a particular position in a native sequence. Immediately adjacent to an amino acid means connected to either the α-carboxyl or α-amino functional group of the amino acid. "Deletional" variants are those with one or more amino acids in the native amino acid sequence removed. Ordinarily, deletional variants will have one or two amino acids deleted in a particular region of the molecule.

The term "treatment" as used herein refers to both therapeutic treatment and prophylactic or preventative measures. It refers to preventing, curing, reversing, attenuating, alleviating, minimizing, suppressing, or halting the deleterious effects of a disease state, disease progression, disease causative agent (e.g., bacteria or viruses), or other abnormal condition.

The term "variants," as used herein, include those polypeptides wherein amino acid residues are inserted into, deleted from, and/or substituted into the naturally occurring (or at least a known) amino acid sequence for the binding agent. Variants of the invention include fusion proteins as described below.

The term "variable" in the context of a variable domain of antibodies refers to certain portions of the pertinent molecule which differ extensively in sequence between and among antibodies and are used in the specific recognition and binding of a particular antibody for its particular target. However, the variability is not evenly distributed through the variable domains of antibodies. The variability is concentrated in three segments called complementarity determining regions (CDRs; i.e., CDR1, CDR2, and CDR3) also known as hypervariable regions, both in the light chain and the heavy chain variable domains. The more highly conserved portions of variable domains are called the framework (FR) regions or sequences. The variable domains of native heavy and light chains each comprise four FR regions, largely adopting a β-sheet configuration, connected by three CDRs, which form loops connecting, and in some cases forming part of, the β-sheet structure. The CDRs in each chain are held together often in proximity by the FR regions and, with the CDRs from the other chain, contribute to the formation of the target (epitope or determinant) binding site of antibodies.

2. ANTIBODY TYPES AND COMPONENTS

Antibodies and antibody fragments that specifically bind CTLA-4 and GLUT2 polypeptides are within the scope of the invention disclosed herein. The antibodies may be monoclonal (mAbs), recombinant, chimeric, or humanized embodiments thereof such as CDR-grafted antibodies, or human, single chain, catalytic, multi-specific and/or bi-specific embodiments thereof, as well as fragments, variants, and/or derivatives thereof.

Alternatively, transgenic animals (e.g., mice) that are capable of producing a repertoire of antibodies in the absence of endogenous immunoglobulin production can be used to generate such antibodies. This can be accomplished by immunization of the animal with a CTLA-4 or GLUT2 antigen or fragments thereof where the CTLA-4 or GLUT2 fragments have an amino acid sequence that is unique to CTLA-4 or GLUT2. Such immunogens can be optionally conjugated to a carrier. Antibodies may also be produced by the expression of recombinant DNA in host-cells or by expression in hybridoma cells as described herein.

Antibodies of the invention may be described or specified in terms of the epitopes or portions of CTLA-4 or GLUT2 that the antibody recognizes or specifically binds. The epitopes or polypeptide portions may be specified as described herein, e.g., by N-terminal and C-terminal positions, by size in contiguous amino acid residues, conformational epitopes and so on.

Antibody fragments that recognize specific epitopes may be generated by known techniques. Traditionally, these fragments were derived via proteolytic digestion of intact antibodies. For example, Fab and F(ab')$_2$ fragments of the invention may be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the $C_{H1}$ domain of the heavy chain. However, those fragments can be produced directly by recombinant host cells. For example, the antibody fragments can be isolated from an antibody phage library. According to another approach, F(ab')$_2$ fragments can be isolated directly from recombinant host cell culture. Other techniques for the production of antibody fragments will be apparent to the skilled practitioner. In other embodiments, the antibody of the invention is a single chain Fv fragment (Fv).

To determine whether a particular antibody homolog binds to a CTLA-4 or GLUT2 polypeptide, any conventional binding assay may be used. Useful binding assays include FACS analysis, ELISA assays, Surface Plasmon Resonance, radio-immunoassays, and the like, which detect antibody binding and functions resulting therefrom, to a CTLA-4 or GLUT2 polypeptide. Full-length and soluble forms of CTLA-4 or GLUT2 polypeptides are useful in such assays. The binding of an antibody or homolog to CTLA-4 or GLUT2, or to soluble fragments thereof, may conveniently be detected through the use of a second antibody specific for immunoglobulins of the species from which the antibody or homolog is derived.

To determine whether a particular antibody or homolog significantly blocks binding to CTLA-4 or GLUT2, any suitable competition assay may be used. Useful assays include, for example, ELISA assays, FACS assays, radioimmunoassays, and the like that quantify the ability of the antibody or homolog to compete with CTLA-4 or GLUT2.

3. VARIANTS OF ANTIBODIES

Variants of antibodies of the invention include insertion, deletion, and/or substitution variants. In one aspect of the invention, insertion variants are provided wherein one or more amino acid residues supplement an antibody amino acid sequence. Insertions may be located at either or both termini of the protein, or may be positioned within internal regions of the antibody amino acid sequence. Insertional variants with additional residues at either or both termini can include, for example, fusion proteins and proteins including amino acid tags or labels. Insertion variants also include antibody polypeptides wherein one or more amino acid residues are added to an antibody amino acid sequence, or fragment thereof.

In still another aspect, the invention provides substitution variants of proteins particularly antibodies of the invention. Substitution variants are generally considered to be "similar" to the original polypeptide or to have a certain "percent identity" to the original polypeptide, and include those polypeptides wherein one or more amino acid residues of a polypeptide are removed and replaced with alternative residues. Relating to a CTLA-4 or GLUT2 antibody in particular, percent identity refers to percent identity outside of the complimentary determining regions of the antibody. In one aspect, the substitutions are conservative in nature; however, the invention embraces substitutions that are also non-conservative.

Antibody fragments include those portions of the antibody that bind to an epitope on the antigen polypeptide. Examples of such fragments include Fab and F(ab')$_2$ fragments generated, for example, by enzymatic or chemical cleavage of full-length antibodies. Other binding fragments include those generated by recombinant DNA techniques, such as the expression of recombinant plasmids containing nucleic acid sequences encoding antibody variable regions. The invention also embraces polypeptide fragments of a CTLA-4 or GLUT2 antibody wherein the fragments maintain the ability to specifically bind a CTLA-4 or GLUT2 polypeptide. Fragments comprising at least 5, 10, 15, 20, 25, 30, 35, 40, 45 or 50 or more consecutive amino acids of a peptide or polypeptide of the invention are comprehended herein. Preferred polypeptide fragments display specific binding and particularly immunological properties unique to or specific for the antigen-binding agent of the invention. Fragments of the invention having the desired specific binding and particularly immunological properties can be prepared by any of the methods well known and routinely practiced in the art.

The antibody fragments and functional equivalents comprising certain embodiments of the invention as disclosed herein encompass those molecules with a detectable degree of specific binding to CTLA-4 or GLUT2. A detectable degree of binding includes all values in the range of at least 10-100%, preferably at least 50%, 60% or 70%, more preferably at least 75%, 80%, 85%, 90%, 95% or 99% of the binding ability of an antibody of interest. Also included are equivalents with an affinity greater than 100% that of an antibody of interest.

The CDRs generally are of importance for epitope recognition and antibody binding. However, in certain instances changes may be made to residues that comprise the CDRs without interfering with the ability of the antibody to recognize and to bind the cognate epitope. For example, changes that do not impact epitope recognition, yet increase the binding affinity of the antibody for the epitope, can be made. Several studies have surveyed the effects of introducing one or more amino acid changes at various positions in the sequence of an antibody, based on the knowledge of the primary antibody sequence, on the properties thereof, such as binding and level of expression.

Thus, equivalents of an antibody of interest can be generated by changing the sequences of the heavy and light chain genes in the CDR1, CDR2 or CDR3, or framework regions, using methods such as oligonucleotide-mediated site-directed mutagenesis, cassette mutagenesis, error-prone PCR, DNA shuffling or mutator-strains of E. coli. The methods of changing the nucleic acid sequence of the primary antibody can result in antibodies with improved binding specificity, for example.

Antibodies with homologous sequences are those antibodies with amino acid sequences that have sequence identity with the amino acid sequence of a CTLA-4 or GLUT2 antibody of the invention, particularly in one, two or three CDR portions of the protein amino acid sequence. Preferably, identity homology is with the amino acid sequence of the variable regions of an antibody of the invention. "Sequence identity" as applied to an amino acid sequence herein is defined as a sequence with at least about 90%, 91%, 92%, 93%, 94% or more sequence identity, and more preferably at least about 95%, 96%, 97%, 98% or 99% sequence identity to another amino acid sequence, as determined, for example, by the.

Preferred methods to determine the relatedness or percent identity of two polypeptides are designed to give the largest match between the sequences tested. Methods to determine identity are described in publicly available computer programs. Preferred computer program methods to determine identity between two sequences include, but are not limited to, the GCG program package, including GAP (Genetics Computer Group, University of Wisconsin, Madison, Wis.), BLASTP, BLASTN, and FASTA. The BLASTX program is publicly available from the National Center for Biotechnology Information (NCBI) and other sources. The well-known Smith Waterman algorithm may also be used to determine identity.

As used herein, the twenty conventional amino acids and their abbreviations follow conventional usage.

The amino acids may have either L or D stereochemistry (except for Gly, which is neither L nor D) and the polypeptides and compositions of the invention may comprise a combination of stereochemistries. However, the L stereochemistry is preferred.

Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the invention. Examples of unconventional amino acids include, without limitation: aminoadipic acid, beta-alanine, beta-aminopropionic acid, aminobutyric acid, piperidinic acid, aminocaprioic acid, aminoheptanoic acid, aminoisobutyric acid, aminopimelic acid, diaminobutyric acid, desmosine, diaminopimelic acid, diaminopropionic acid, N-ethylglycine, N-ethylasparagine, hydroxylysine, allo-hydroxylysine, hydroxyproline, isodemosine, allo-isoleucine, N-methylglycine, sarcosine, N-methylisoleucine, N-methylvaline, norvaline, norleucine, orithine, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and amino acids (e.g., 4-hydroxyproline).

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences."

Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Even more substantial modification in an antibody range and presentation of biological properties can be accomplished by selecting an amino acid that differs more substantially in properties from that normally resident at a site. Thus, such a substitution can be made while maintaining: (a) the structure of the polypeptide backbone in the area of the substitution, for example, as a sheet or helical conformation; (b) the charge or hydrophobicity of the molecule at the target site, or (c) the bulk of the side chain.

Naturally occurring residues may be divided into classes based on common side chain properties:
1) hydrophobic: Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

Preferred amino acid substitutions include those which: (1) reduce susceptibility to proteolysis, (2) reduce susceptibility to oxidation, (3) alter binding affinity and (4) confer or modify other physico-chemical or functional properties of such analogs. Analogs can include various muteins of a sequence other than the naturally occurring peptide sequence. For example, single or multiple amino acid substitutions (preferably conservative amino acid substitutions) may be made in the naturally occurring sequence (preferably in the portion of the polypeptide outside the domain (s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence) unless of a change in the bulk or conformation of the R group or side chain.

For example, non-conservative substitutions may involve the exchange of a member of one of these classes for a member from another class. Such substituted residues may be introduced into regions of the antibody that are homologous with antibodies to other orthologs, or into the non-homologous regions of the molecule.

Antibodies comprising certain embodiments of this invention that are polypeptide or peptide substitution variants may have up to about ten to twelve percent of the original amino acid sequence replaced. For antibody variants, the heavy chain may have 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 amino acid replaced, while the light chain may have 25, 24, 23, 22, 21, 20, 19, 18, 17, 16, 15, 14, 13, 12, 11, 10, 9, 8, 7, 6, 5, 4, 3, 2, or 1 amino acid replaced.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity; particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One may also identify epitopes from primary amino acid sequences on the basis of hydrophilicity. These regions are also referred to as "epitopic core regions."

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

In certain embodiments, antibody variants include glycosylation variants wherein the number and/or type of glycosylation site has been altered compared to the amino acid sequences of the parent polypeptide. In certain embodiments, protein variants comprise a greater or a lesser number of N-linked glycosylation sites than the native protein. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

The functional equivalents of the present application also include modified antibodies, e.g., antibodies modified by the covalent attachment of any type of molecule to the antibody. For example, modified antibodies include antibodies that have been modified, e.g., by glycosylation, acetylation, pegylation, deamidation, phosphorylation, amidation, derivatization by known protecting/blocking groups, proteolytic cleavage, linkage to a cellular ligand, linkage to a toxin or cytotoxic moiety or other protein. The covalent attachment need not yield an antibody that is immune from generating an anti-idiotypic response. The modifications may be achieved by known techniques, including, but not limited to, specific chemical cleavage, acetylation, formylation, or metabolic synthesis. Additionally, the modified antibodies may contain one or more non-classical amino acids.

4. PHARMACEUTICAL COMPOSITIONS

Pharmaceutical compositions of the disclosed proteins of the invention are within the scope of the invention as disclosed herein. Pharmaceutical compositions comprising antibodies are described generally in the art. Such compositions comprise a therapeutically or prophylactically effective amount of a protein, particularly an antibody or a specific binding fragment thereof, variant, derivative or fusion thereof as described herein, in admixture with a pharmaceutically acceptable agent.

Therapeutic formulations of the protein particularly antibodies or a specific binding fragments thereof may be prepared for storage as lyophilized formulations or aqueous solutions by mixing a protein particularly antibodies or a specific binding fragments thereof having the desired degree of purity with optional "pharmaceutically acceptable" carriers, diluents, excipients or stabilizers typically employed in the art, i.e., buffering agents, stabilizing agents, preservatives, isotonifiers, non-ionic detergents, antioxidants and other miscellaneous additives. Such additives are generally nontoxic to the recipients at the dosages and concentrations employed, hence, the excipients, diluents, carriers and so on are pharmaceutically acceptable.

Formulation of the proteins particularly antibodies or a specific binding fragments thereof disclosed herein also may contain more than one active compound as necessary for the particular indication being treated, preferably those with complementary activities that do not adversely impact each other. For example, it may be desirable to further provide an immunosuppressive agent. Such molecules suitably are present in combination in amounts that are effective for the purpose intended.

Non-ionic surfactants or detergents (also known as "wetting agents") may be added to help solubilize the therapeutic agent, as well as to protect the therapeutic protein against agitation-induced aggregation, which also permits the formulation to be exposed to shear surface stresses without causing denaturation of the protein. Suitable non-ionic surfactants include polysorbates (e.g., 20, 80), polyoxamers (e.g., 184, 188), Pluronic® polyols and polyoxyethylene sorbitan monoethers (e.g., TWEEN-20®, TWEEN-80®). Non-ionic surfactants may be present in a range of about 0.05 mg/ml to about 1.0 mg/ml, preferably about 0.07 mg/ml to about 0.2 mg/ml.

The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants.

Optimal pharmaceutical composition can be appreciated by one skilled in the art depending upon, for example, the intended route of administration, delivery format, and desired dosage. Such compositions may influence the physical state, stability, rate of in vivo release, and rate of in vivo clearance of the protein particularly antibodies or a specific binding fragments thereof.

The primary vehicle or carrier in a pharmaceutical composition may be either aqueous or non-aqueous in nature. For example, a suitable vehicle or carrier may be water for injection, physiological saline solution possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute therefore. In one embodiment of the invention, protein compositions may be prepared for storage by mixing the selected composition having the desired degree of purity with optional formulation agents in the form of a lyophilized cake or an aqueous solution. Further, the antibody product may be formulated as a lyophilizate using appropriate excipients such as sucrose.

Particular embodiments of the invention encompass liquid formulations having stability at temperatures found in a commercial refrigerator and freezer found in the office of a physician or laboratory, such as from about −20° C. to about 5° C., said stability assessed, for example, by high performance size exclusion chromatography (HPSEC), for storage purposes, such as for about 60 days, for about 120 days, for about 180 days, for about a year, for about 2 years or more. The liquid formulations of the invention also exhibit stability, as assessed, for example, by HSPEC, at room temperatures, for at least a few hours, such as one hour, two hours or about three hours prior to use.

Pharmaceutical compositions as provided herein can be selected for parenteral delivery. The preparation of such pharmaceutically acceptable compositions is within the skill of the art.

The formulation components are present in concentrations that are acceptable to the site of administration. For example, buffers are used to maintain the composition at physiological pH or at slightly lower pH, typically within a pH range of from about 5 to about 8.

When parenteral administration is contemplated, the therapeutic compositions for use in this invention may be in the form of a pyrogen-free, parenterally acceptable aqueous solution comprising the desired antibody in a pharmaceutically acceptable vehicle. A particularly suitable vehicle for parenteral injection is sterile distilled water in which a binding agent is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), beads, or liposomes that provides for the controlled or sustained release oϕ the product which may then be delivered via a depot injection. Hyaluronic acid may also be used, and this may have the effect of promoting sustained duration in the circulation. Other suitable means for the introduction of the desired molecule include implantable drug delivery devices.

In a preferred embodiment, an aqueous solution of therapeutic protein including antibodies or specific-binding fragments thereof can be administered by subcutaneous injection. Each dose may range from about 1 mg to about 10 mg per kilogram of body weight. The dosage can be ascertained empirically for the T1D patient population, mode of administration and so on, practicing pharmaceutical methods known in the art.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

For any compound, the therapeutically effective dose can be estimated initially either in cell culture assays or in animal models such as mice, rats, rabbits, dogs, or pigs. An animal model, specifically a NOD mouse model, may also be used to determine the appropriate concentration range and route of administration. Such information can then be used to determine useful doses and routes for administration in humans.

The exact dosage can be determined in light of factors related to the subject requiring treatment. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

The frequency of dosing will depend upon the pharmacokinetic parameters of the binding agent molecule in the formulation used. Typically, a composition is administered until a dosage is reached that achieves the desired effect. The composition may therefore be administered as a single dose or as multiple doses (at the same or different concentrations/dosages) over time, or as a continuous infusion. Further refinement of the appropriate dosage is routinely made. Appropriate dosages may be ascertained through use of appropriate dose-response data.

To prolong the serum circulation of an antibody in vivo, various techniques can be used. For example, inert polymer molecules, such as high molecular weight polyethylene glycol (PEG), can be attached to an antibody with or without a multifunctional linker either through site-specific conjugation of the PEG to the N-terminus or to the C-terminus of the antibody or via $\epsilon$ amino groups present on lysine residues. Linear or branched polymer derivatization that results in minimal loss of biological activity can be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion exchange chromatography. PEG-derivatized antibodies can be tested for binding activity as well as for in vivo efficacy using methods known to those of skilled in the art, for example, by immunoassays described herein.

An antibody having an increased half-life in vivo can also be generated by introducing one or more amino acid modifications (i.e., substitutions, insertions or deletions) into an IgG constant domain, or $F_cR$ binding fragment thereof (such as an $F_c$ or hinge $F_c$ domain fragment).

Further, an antibody can be conjugated to albumin to make an antibody more stable in vivo or have a longer half-life in vivo. The techniques are known in the art. The antibody also can be modified, for example, by glycosylation, acetylation, phosphorylation, amidation, derivatization by known protecting/blocking groups, proteolytic cleavage, linkage to a cellular ligand or other protein and so on.

EXAMPLES

The invention now will be exemplified for the benefit of the artisan by the following non-limiting examples that depict some of the embodiments by and in which the invention can be practiced.

Example 1

Producing Recombinant GLUT2, Generating and Characterizating Anti-GLUT2 mAbs

Although some antibodies (mainly polyclonal) to mouse GLUT2 are commercially available, there is no disclosure on whether those antibodies would possess antagonistic or neutralizing activities for GLUT2 activity (i.e., regarding whether they would interfere with glucose transporter activity), in which case they cannot be used as part of an antibody that binds both GLUT2 and CTLA-4 for therapy. Therefore, there is a need in the art for anti-GLUT2 mAbs that do not interfere with GLUT2 glucose transport activity. Although GLUT2 is a transmembrane protein, an antibody that recognizes only its 67 amino acid ectoplasmic domain would be beneficial because the antibody would be able to bind to an extracellular epitope expressed specifically on the surface of pancreatic $\beta$-cells.

To ensure display of native epitopes and to retain native conformation, both full length GLUT2 (FL) and its ectodomain (Ecto) region were produced. The cDNA corresponding to the ecto-GLUT2 (~200 bp) was PCR amplified using primers having the sequence:

```
                                    (SEQ ID NO.: 02)
5'-GCGCCATATGAATGCACCTCAAGAGGTAATAATA-3'
and (SEQ ID NO.: 03)
5'-GCGCGGATCCTTAAGACCAGAGCATAGTGACTATGTG-3'.
```

The ecto-GLUT2 was cloned into an *E. coli* expression vector (pET15b) in frame with the N-terminal 6×His tag coding sequence. Recombinant Ecto-GLUT2 was purified (>95% purity) from *E. coli* lysate by Ni-NTA agarose, followed by reverse phase HPLC, dialyzed and concentrated (FIG. 1, upper panel). The peptide identity was confirmed by mass spectrometry. The FL-GLUT2 cDNA (~1.5 kb) was PCR amplified using primers having the sequence: 5'-GCGCG-GATCCATCAGAAGACAAGATCACCGG-3' (SEQ ID NO.: 04) and 5'-GCGCGAATTCTCACACACTCTCTGAA-GACGC-3' (SEQ ID NO.: 05) and cloned into a mammalian expression vector (pcDNA3.1-HisB) in frame with the coding sequence for an N-terminal 6×His tag. HEK 293 cells were transfected with the plasmid and G418 resistant stable clones were selected. The membrane was solubilized in 2% Tween-20 in 50 mM phosphate buffer and the FL-GLUT2 was purified on a Ni-NTA agarose column and confirmed by western blot using anti-GLUT2 polyclonal antibodies (FIG. 1, lower panel).

Figure 2:
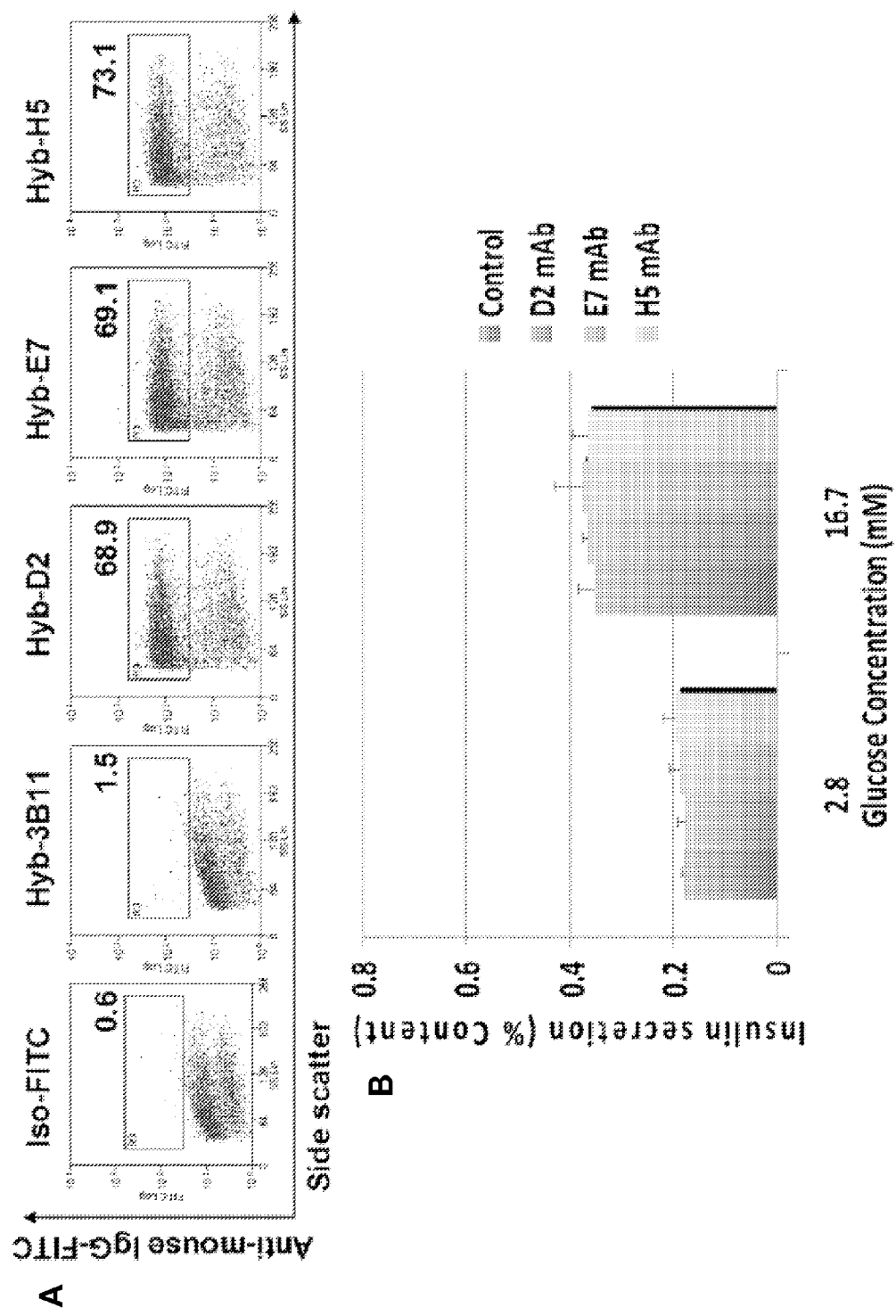
FIG. 2(a) shows fluorescence-activated cell sorting (FACS) analysis of three anti-GLUT mAbs disclosed herein binding to native GLUT2 expressed on Min-6 cells.
FIG. 2(b) shows that anti-GLUT2 mAbs from D2, E7 and H5 hybridoma clones do not interfere with GLUT2 function as a glucose sensor.

In order to generate anti-GLUT2 antibodies, Balb/c mice were repeatedly immunized subcutaneously with 50 mg of purified Ecto-GLUT2 emulsified in complete Freund's adjuvant (CFA) and monitored for anti-Ecto-GLUT2 antibody levels. When animals showed high titers of antibodies (i.e., 1:90,000), they were given a final dose of Ecto-GLUT2 without the adjuvant and were euthanized after 4 days. Splenocytes were then fused to SP2 myeloma cells and selected with hypoxantine/aminopterin/thymidine (HAT) medium. Hybridoma supernatants were tested for the presence of anti-GLUT2 antibodies by ELISA against Ecto-GLUT2. Positive hybridomas were cloned and further screened for anti-GLUT2 IgG by western blot against FL-GLUT2. Three clones (named D2, E7 and H5) were selected that were highly specific for Ecto-GLUT2 and FL-GLUT2 by western blot. These Abs were tested for their capacity to recognize native GLUT2 expressed on the surface of Min-6 cells (a mouse insulinoma cell line) by FACS using a secondary anti-mouse antibody. The 3B11 hybridoma supernatant (non-specific) was used as a negative control. All three anti-GLUT2 monoclonal antibodies recognized native GLUT2 expressed on Min-6 cells (FIG. 2, upper panel).

To test if mAb binding interfered with GLUT2 function, (3-TC-6 (mouse insulinoma cell line) cells were seeded in 96 well plates and incubated overnight with media alone (control) or media plus one of the 3 different purified mAbs (i.e. D2, E7 and H5). Cells were then washed in a modified Krebs-Ringer HEPES buffer (pH=7.4, 0.5% BSA) and insulin secretion was stimulated using Krebs 2.8 mM glucose solution (basal) or 16.7 mM glucose solution for 1 h. The amount of insulin in the incubation buffers and cell extracts were measured using an ultra sensitive mouse-insulin ELISA kit (Crystal Chem INC). Insulin secretion was expressed as a percentage of the total insulin, which was the sum of insulin in basal and stimulated buffers, and cell extracts (FIG. 2, lower panel). Similar insulin secretion in the control and anti-GLUT2 Ab treated cells indicated that none of the mAbs disturbed GLUT2 function.

Figure 3:
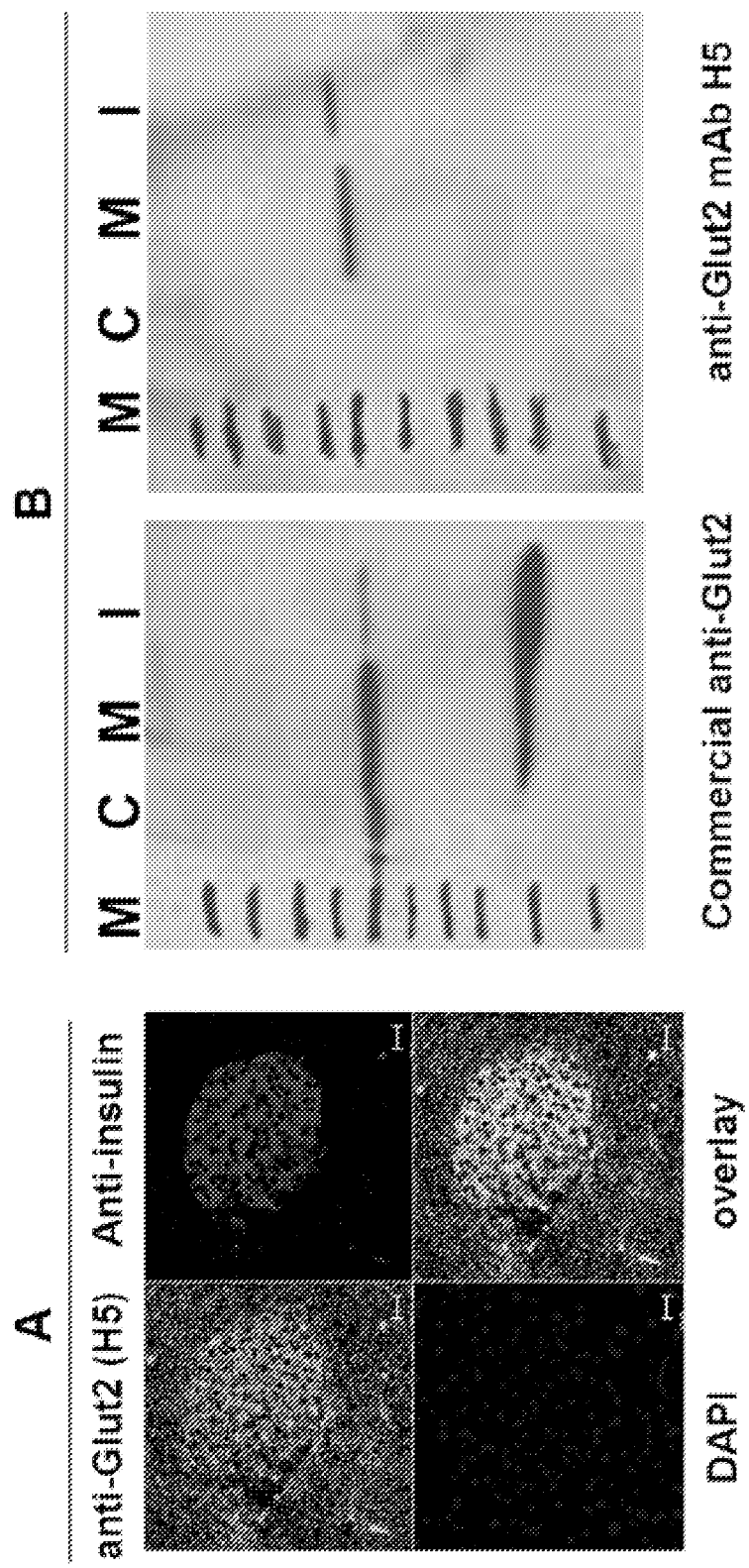
FIG. 3(a) shows that anti-GLUT2, anti-CTLA-4 protein is capable of binding to pancreatic islets in mice.
FIG. 3(b) shows that this protein is able to detect GLUT2 in the membrane fraction of Min-6 (mouse insulinoma cells).

Anti-Glut2 mAb H5 was chosen for initial construction of the anti-CTLA4, anti-GLUT2 protein. This protein was tested for its capacity to bind to mouse pancreatic islets by immunofluorescence (FIG. 3(a)). Anti-insulin staining showed co-localization of anti-GLUT2 and anti-insulin antibodies on pancreatic islets. The H5 mAb was compared with a commercial rabbit anti-GLUT2 Ab (abcam # ab54460) raised against a synthetic peptide derived from the cytoplasmic domain of rat GLUT2, for its binding to endogenous GLUT2 expressed in Min-6 cells in Western Blots (FIG. 3(b)). The commercial Ab reacted with membrane bound as well as the membrane bound GLUT2.

Example 2

Constructing an Anti-GLUT2, Anti-CTLA-4 Protein

Figure 4:
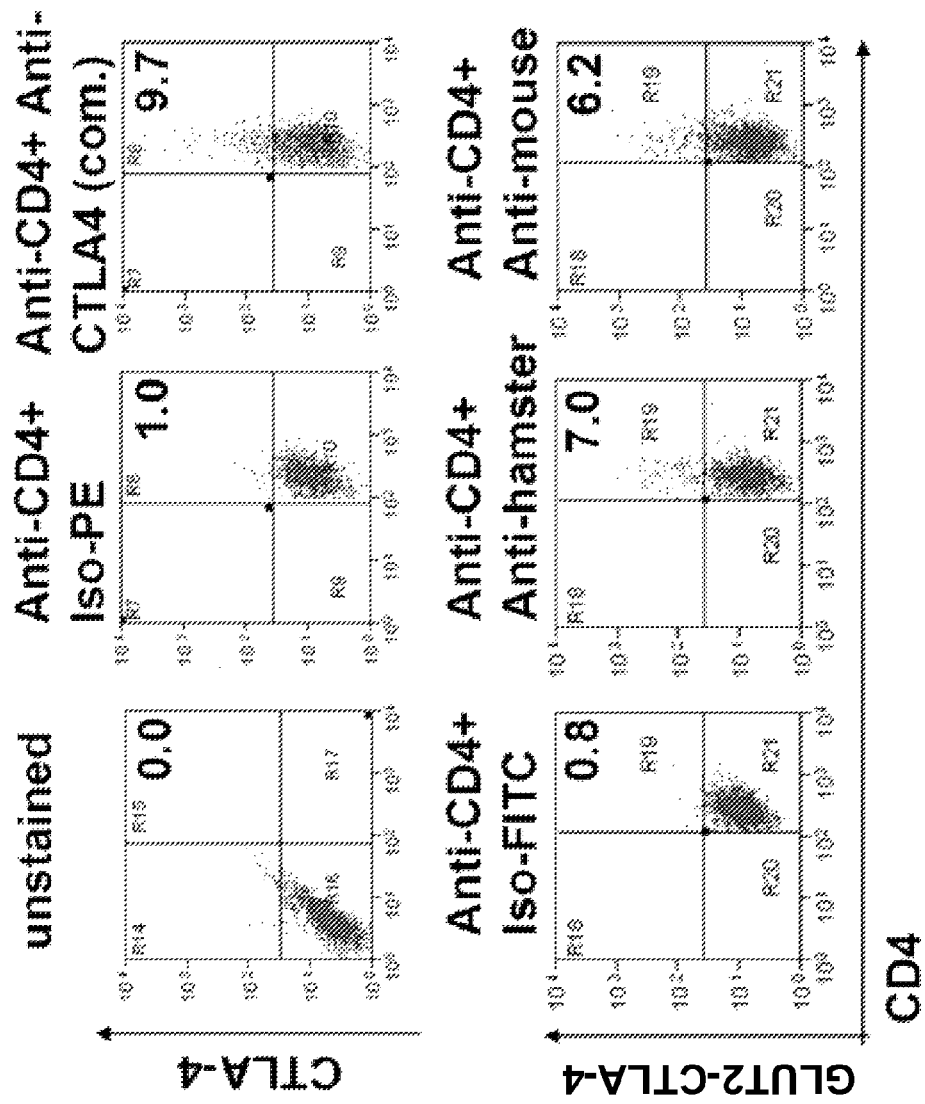
FIG. 4 shows FACS analysis indicating that anti-GLUT2, anti-CTLA-4 protein is capable of binding CTLA-4 on $CD4^+$ T-cells.
Figure 5:
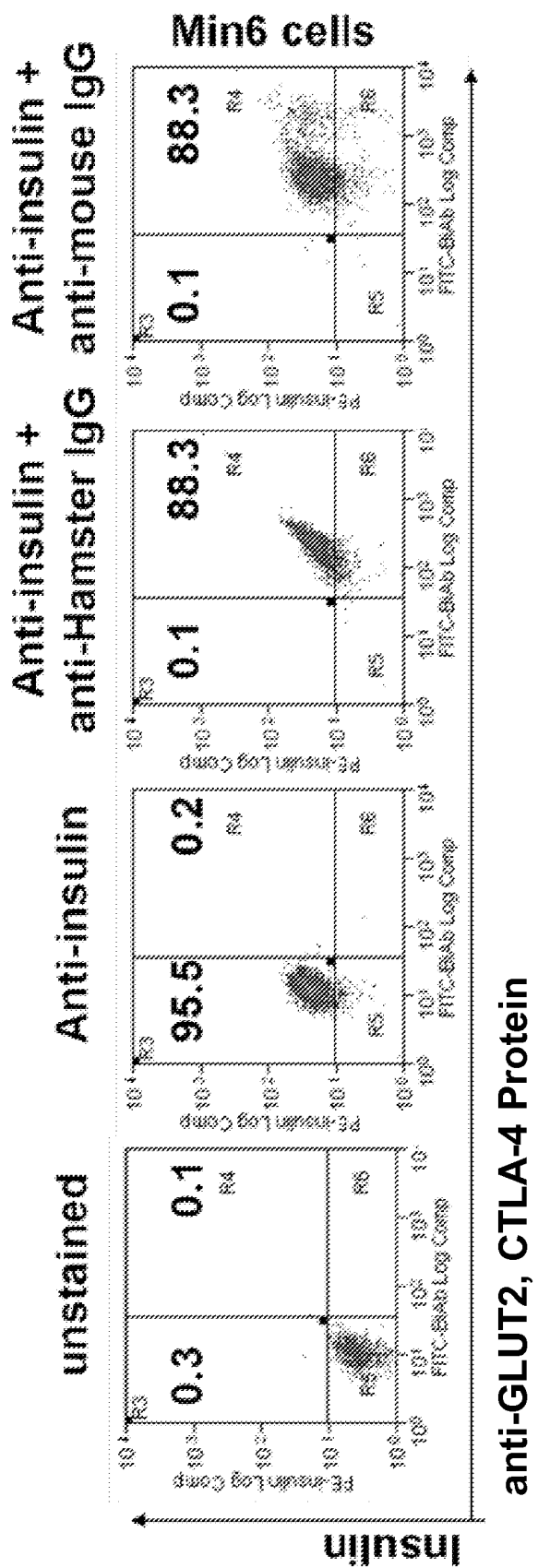
FIG. 5 shows FACS analysis indicating that anti-GLUT2, anti-CTLA-4 protein is capable of binding to GLUT2 on Min-6 cells.

Hamster anti-CTLA-4 Ig (hybridoma UC10 B-4-F-10-11; ATCC, Rockville, Md.) was purified using protein-A agarose beads. Purified anti-GLUT2 (H5) and anti-CTLA-4 IgGs were chemically coupled using Pierce Protein-Protein Cross-linking Kit to generate the protein, which was then followed by purification. The anti-CTLA4, anti-GLUT2 protein was used to stain mouse splenocytes and Min-6 insulinoma cells, and probed with anti-mouse and anti-hamster secondary Abs. Splenocytes and Min-6 cells were co-stained with anti-CD4 and anti-insulin Abs respectively. Approximately 9.7% of the CD4$^+$ T cells were double positive for CD4 and CTLA-4 expression (FIG. 4, upper right panel) which was comparable to that detected using the anti-CTLA-4, anti-GLUT2 protein (FIG. 4, lower middle and right panels). FACS analysis also revealed that nearly 90% of the Min-6 cells were double positive for insulin and GLUT2 expression as detected by a control as well as the anti-CTLA4, anti-GLUT2 protein (FIG. 5). These results showed that the anti-CTLA4, anti-GLUT2 protein can bind to native CTLA-4 and GLUT2 expressed on the cell membrane.

Example 3

Figure 6:
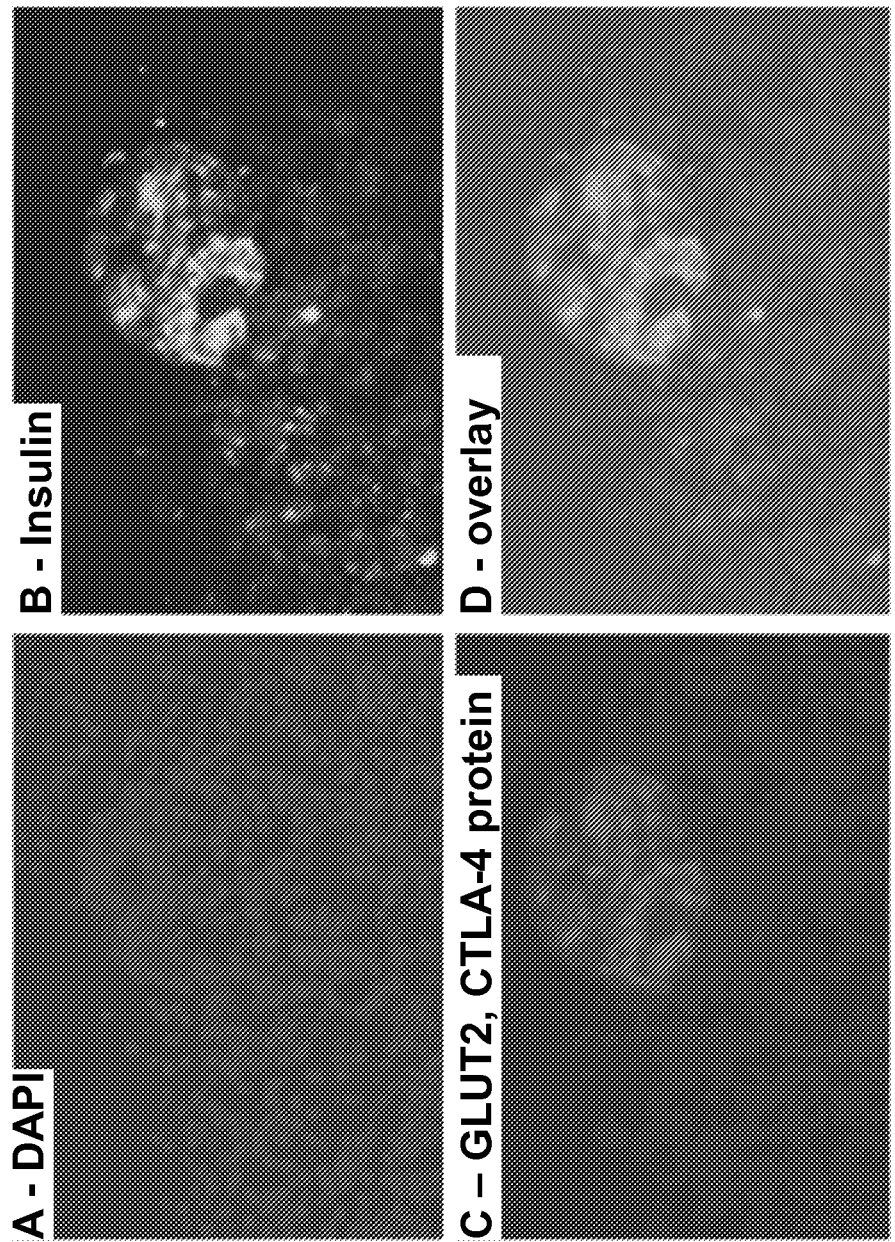
FIG. 6 shows that anti-GLUT2, anti-CTLA-4 protein is capable of binding to insulin producing islet cells in vivo.

Examining the Ability of an Anti-Glut2, Anti-CTLA-4 Protein to Target β-Cells and Suppress Activated T-Cells In Vivo While infiltrating T-cells recognize β-cell specific antigens through T-cell receptors and migrate to islets of Langerhans in the pancreas, anti-GLUT2, anti-CTLA-4 protein engages CTLA-4 on infiltrating T-cells. This process leads to suppression of effector T-cell function and generation of β-cell specific Tregs which inhibit the autoimmune effector T-cells from destroying β-cells. Thus, the efficacy of the anti-GLUT2, anti-CTLA-4 protein depends on how efficiently it can bind to GLUT2 expressing pancreatic β-cells. The anti-GLUT2, anti-CTLA-4 protein was tested to determine if it is capable of homing to β-cells by administering injections and performing immunohistochemistry on pancreatic tissue. To test this efficacy, 100 µg purified anti-CTLA4, anti-GLUT2 protein was injected intravenously into CB17-SCID mice (devoid of endogenous Igs), and the pancreas harvested after 3 hours. Direct immunoflurescence staining using an anti-mouse secondary Ab showed that anti-CTLA4, anti-GLUT2 protein can bind to insulin secreting pancreatic islet cells in vivo (FIG. 6).

Example 4

Analysis of Anti-GLUT2, Anti-CTLA-4 Protein Associated Pathology

Figure 7:
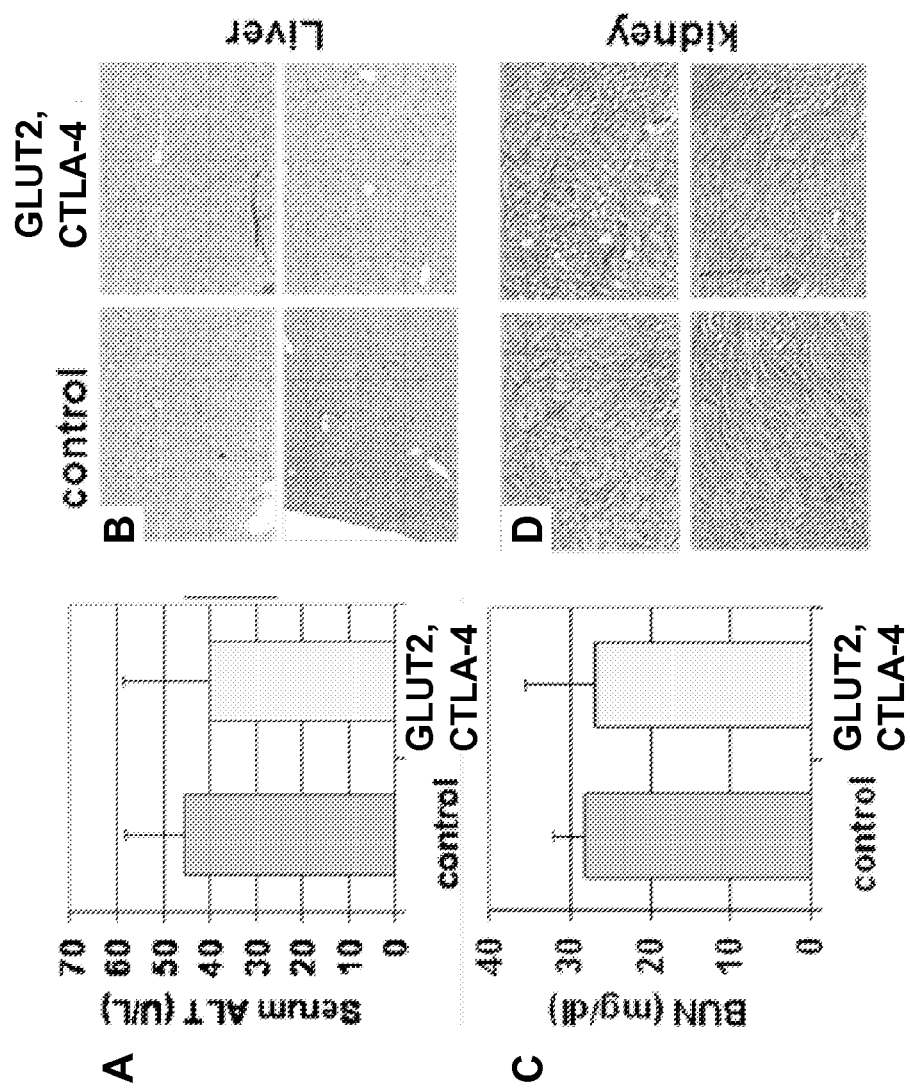
FIG. 7(a)-(d) shows that treatment of NOD mice with anti-GLUT2, anti-CTLA-4 protein did not cause interference of liver or kidney functions.

To ensure that anti-CTLA4, anti-GLUT2 protein can be used safely without harmful side-effects, 6-week old NOD mice were treated three times with 100 ug of the anti-GLUT2, anti-CTLA-4 protein at 2-week intervals. Blood sugar was monitored weekly to assess deregulation in glucose metabolism as an indicator of perturbation in GLUT2 function. Through the end of a 10-week period, both groups of treated mice failed to show any perturbation in glucose levels as compared to untreated controls. The sera from these NOD mice were then tested for Alanine Aminotransferase (ALT), (FIG. 7(a)) and Blood Urea Nitrogen (BUN), (FIG. 7(c)) to detect to detect damage to hepatocytes and kidney respectively. These results showed no difference in the levels of these markers (FIGS. 7(a) and 7(c)) between control and the anti-CTLA4, anti-GLUT2 protein-treated groups. Histopathological examination of the liver and kidney tissues from these mice also failed to reveal any damage (FIGS. 7(b) and 7(d)). These results indicate that no harmful effects result from the treatment, and that an anti-CTLA4, anti-GLUT2 protein can be used safely without any apparent off target effects.

Example 5

Figure 8:
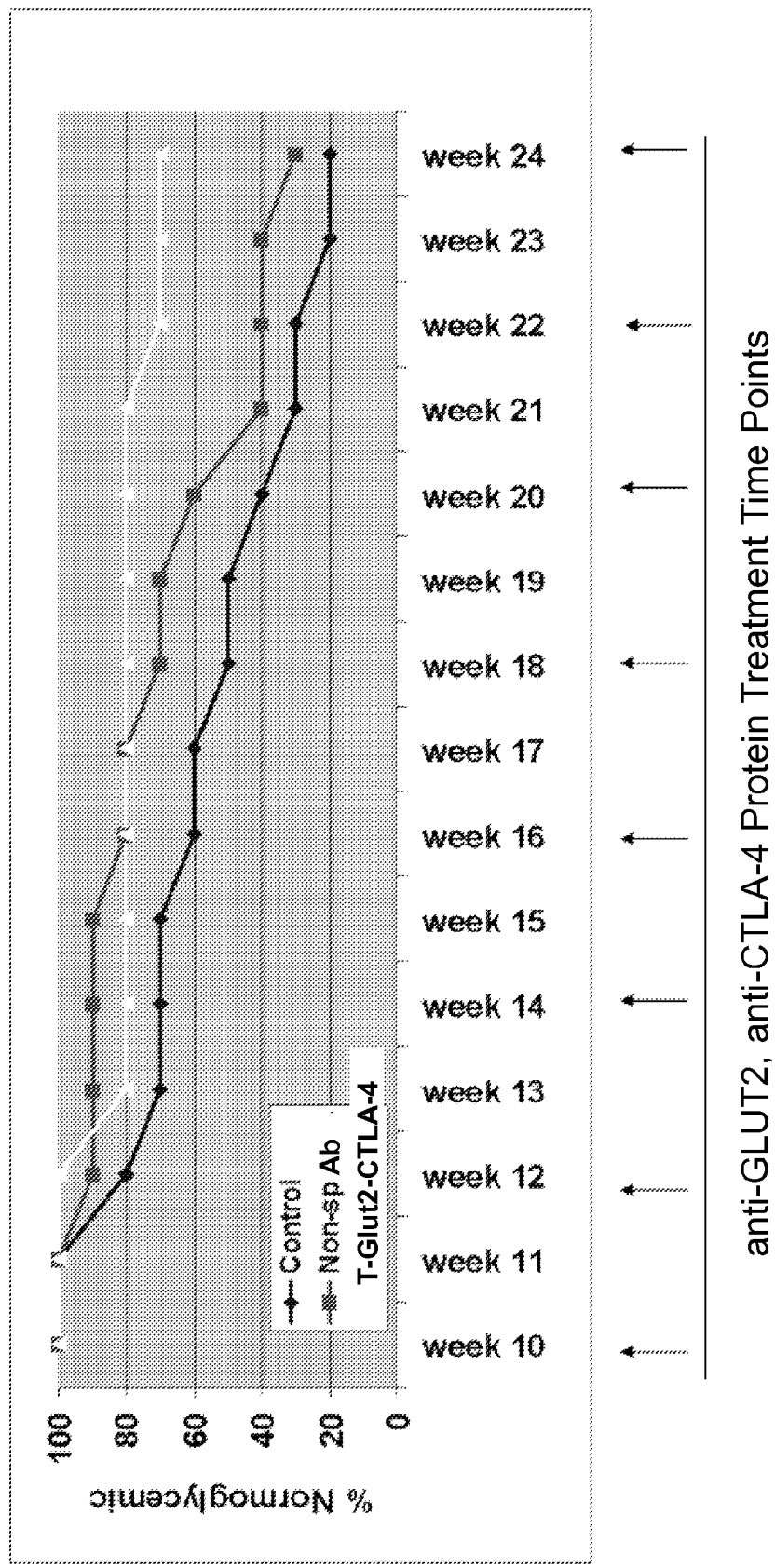
FIG. 8 shows effects of biweekly anti-GLUT2, anti-CTLA-4 protein treatment of NOD mice started at age 10 weeks.
Figure 9:
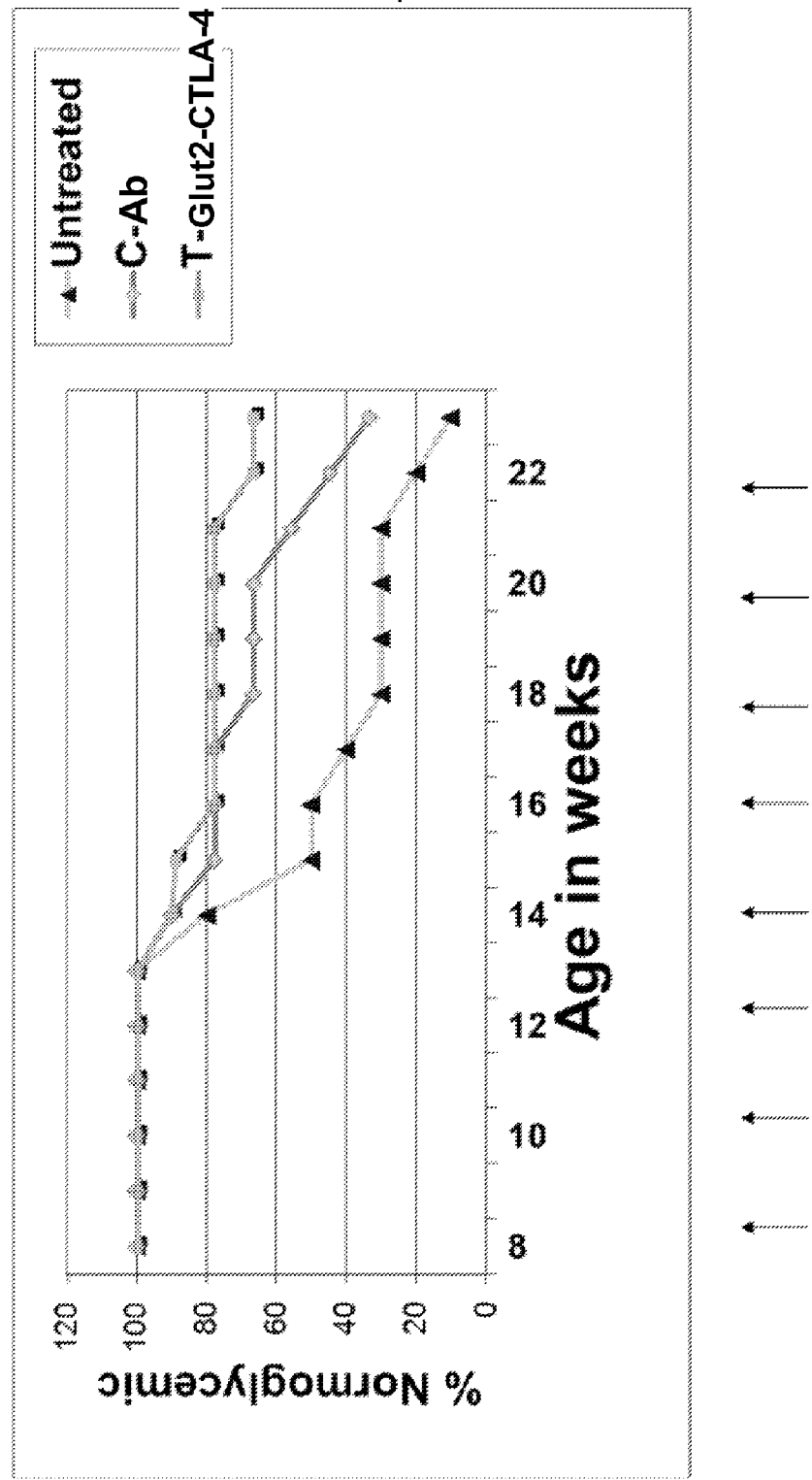
FIG. 9 shows effects of biweekly anti-GLUT2, anti-CTLA-4 protein treatment of NOD mice started at age 8 weeks.
Figure 10:
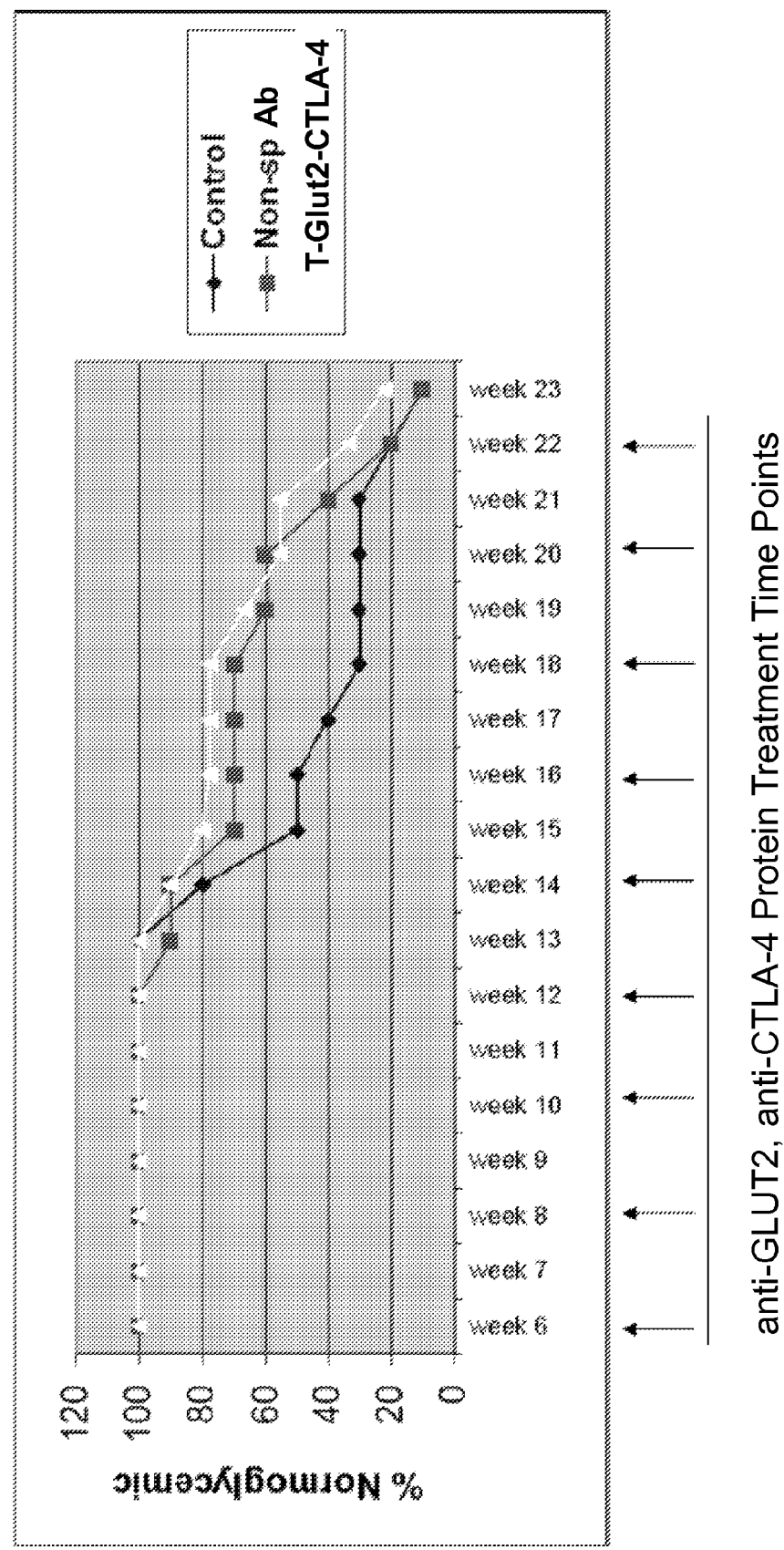
FIG. 10 shows effects of biweekly anti-GLUT2, anti-CTLA-4 protein treatment of NOD mice started at age 6 weeks.
Figure 11:
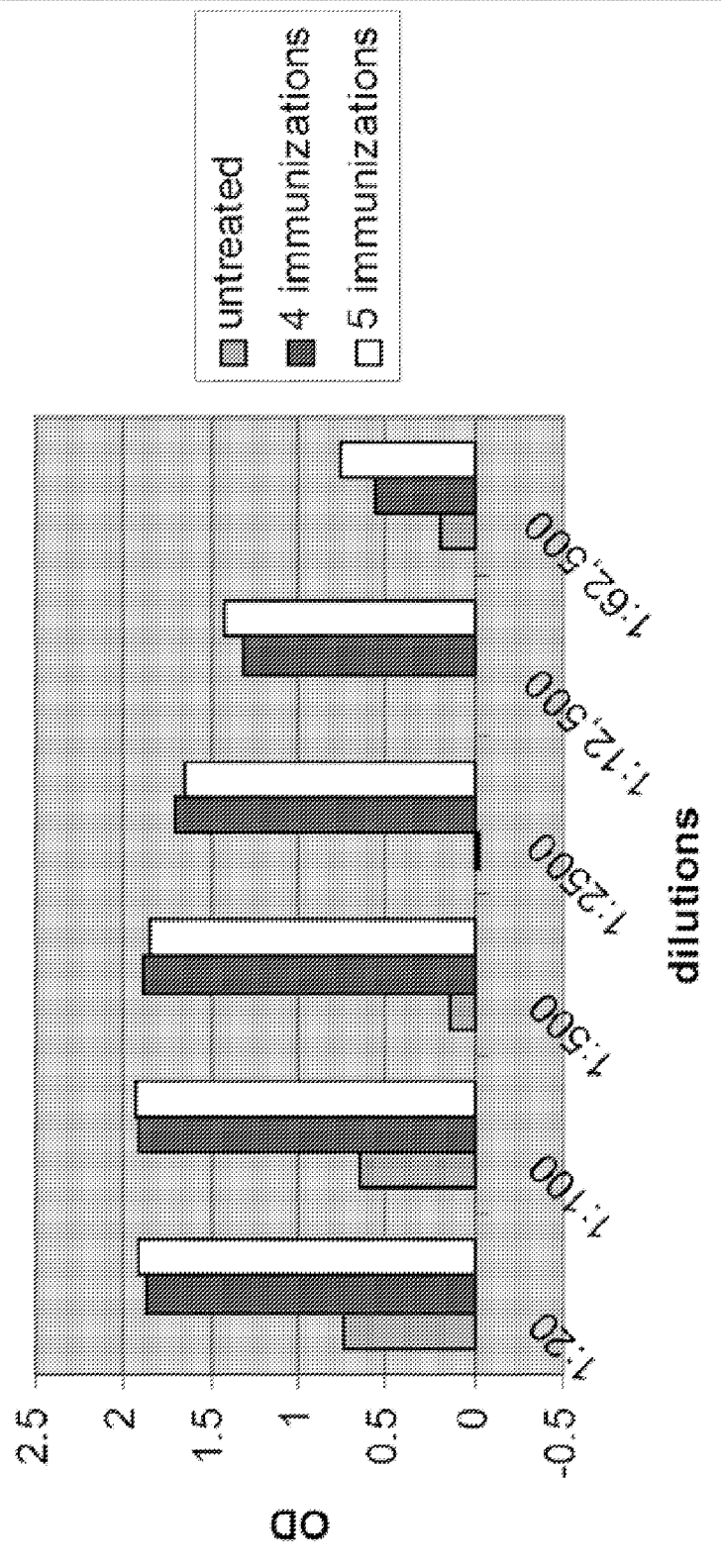
FIG. 11 shows a comparison between anti-hamster IgG response in 8 week and 6 week anti-GLUT2, anti-CTLA-4 protein treatment in NOD mice.

Determination of Therapeutic Potential of Anti-GLUT2, Anti-CTLA-4 Protein in Preventing Type 1 Diabetes To determine the efficacy (whether treatment can stabilize the glucose levels or reverse ongoing diabetes) of the anti-GLUT2, anti-CTLA-4 protein treatment in mice at various stages of disease, groups of mice at starting at 6, 8 and 10 weeks of age were treated with anti-GLUT2, anti-CTLA-4 protein (100 µg/mouse/dose, referred in FIGS. 7-12 as T-Glut2-CTLA-4) every two weeks until at least 23 weeks of age and monitored for disease progression as indicated by increasing blood glucose levels. The results were compared against one group of untreated mice (referred in the FIGS. 7-12 as control or untreated) and one group of mice treated with a non-specific mAb, anti-CTLA-4 protein (referred in the FIGS. 7-12 as C-Ab or Non-sp Ab). The best protective effect was seen when the treatment was initiated at 10-weeks of age (FIG. 8), followed by initiation of treatment at 8-weeks age (FIG. 9); followed by initiation of treatment at 6 weeks of age (FIG. 10). These results show that anti-GLUT2, anti-CTLA-4 protein therapy can delay development of hyperglycemia in NOD mice. Table 1 shows summary of the results (therapeutic efficacy of biweekly anti-GLUT2, anti-CTLA-4 protein treatment of NOD mice started at 6 weeks, 8 weeks and 10 weeks of age).

TABLE 1

| Group | Hyperglycemic at 15-Week | p-value* | Hyperglycemic at 19-Week | p-value* | Hyperglycemic at 23-Week | p-value* |
|---|---|---|---|---|---|---|
| Control | 5/10 | | 7/10 | | 9/10 | |
| 6-Week Non-sp Ab | 3/10 | 0.36 | 4/10 | 0.18 | 9/10 | 1 |
| 6-Week Glut2-CTLA-4 protein | 1/9 | 0.069 | 3/9 | 0.11 | 7/9 | 0.47 |
| 8-Week Non-sp Ab | 2/10 | 0.16 | 3/9 | 0.11 | 6/9 | 0.21 |
| 8-Week Glut2-CTLA-4 protein | 1/9 | 0.069 | 2/9 | 0.04 | 3/9 | 0.01 |
| Control | 3/10 | | 5/10 | | 8/10 | |
| 10-Week Non-sp Ab | 1/10 | 0.26 | 3/10 | 0.36 | 6/10 | 0.33 |
| 10-Week Glut2-CTLA-4 protein | 2/10 | 0.61 | 2/10 | 0.16 | 3/10 | 0.02 |

*p-value is calculated against the control group.

These results indicated that the anti-CTLA-4 mAb is a hamster antibody and thus will be immunogenic in the recipient mice. Therefore, the more times the treatment is administered, the higher the resultant anti-hamster antibody titer (see FIG. 11). Evidently, the anti-hamster antibodies thus elicited in recipient NOD mice can neutralize the effect of subsequent anti-GLUT2, anti-CTLA-4 protein treatments. Since the 6, 8 and 10 week old recipients received 4, 3 and 2 anti-GLUT2, anti-CTLA-4 protein treatments respectively, prior to onset of diabetes, the 10 week study showed the highest efficacy. This problem can be readily overcome by using a mouse anti-CTLA-4 IgG.

Example 6

Stability and Persistence of Anti-GLUT2, Anti-CTLA-4 Protein Binding

To test the stability of anti-GLUT2, anti-CTLA-4 protein in vitro, normal mouse sera are spiked with anti-GLUT2, anti-CTLA-4 protein at day 0. Spiked sera are incubated at 37° C. for 7 days. Samples are then taken out every 24 hours and stored at −20° C. After 7 days, all samples are analyzed by ELISA against FL-GLUT2 to measure any loss of Ab integrity. The capacity of the Abs to simultaneously recognize CTLA-4 and GLUT2 is determined by FACS as described above for FIG. 4.

To test the stability and persistence of anti-GLUT2, anti-CTLA-4 protein binding in vivo, 4 groups of 3 mice each are given a single intravenous dose of 100 μg anti-GLUT2, anti-CTLA-4 protein. One group of mice is euthanized at different time-points (1, 2, 4, and 8 days post-injection) and pancreatic tissue harvested. Fixed pancreatic tissue sections are further incubated with FITC labeled anti-hamster IgG and analyzed to determine the stability and persistence of anti-GLUT2, anti-CTLA-4 protein binding to pancreatic islets in vivo.

Example 7

Analysis of Potential Anti-GLUT2, Anti-CTLA-4 Protein Associated Pathology

Although the in vitro studies showed that the anti-GLUT2 mAb is functionally neutral and mice immunized with GLUT2 to generate hybridomas showed no apparent signs of disease, a comprehensive pathological study of different tissues is performed to ensure lack of pathology. Groups of mice are treated with different doses of the anti-GLUT2, anti-CTLA-4 protein and observed for 2 weeks for weight loss or any sign of distress. Tail bleed is used to monitor blood glucose levels and serum insulin levels. Because GLUT2 acts as a vital glucose sensor in liver, kidney and β-cells, any perturbation of GLUT2 function could destabilize glucose levels and hence insulin release. Additionally, vital organs (brain, liver, kidney, heart and intestine) are harvested and analyzed for tissue damage.

Example 8

Anti-GLUT2, Anti-CTLA-4 Protein Modulation of T-Cell Function In Vivo

The anti-GLUT2, anti-CTLA-4 protein is evaluated for its ability to modulate pathogenic T-cell function in vivo. It has been shown that in vitro activated NOD-BDC2.5 T-cells, as well as T-cells from wild-type NOD mice, can induce hyperglycemia rapidly in young NOD mice and NOD-SCID mice (Bending et al., 2009, *The Journal of Clinical Investigation* 119:565-72; and Wagner et al., 2002, *Proc. Nat. Acad. Sic U.S.A.* 99:3782-7). These adoptive transfer models are used to examine the ability of in vivo injected anti-GLUT2, anti-CTLA-4 protein to modulate pathogenic T-cell function in vivo. In the first set of experiments, spleen cells from NOD- BDC2.5 TCR transgenic mice are activated in vitro using BDC2.5 peptide (YVRPLWVRME, SEQ ID NO.: 06) for 4 days, CD4$^+$ cells purified, labeled using Carboxyfluorescein succinimidyl ester (CFSE), and injected ($1\times10^6$ T-cells/mouse) intravenously into control antibody- and anti-GLUT2, anti-CTLA-4 protein-treated young (3-4 week old) NOD mice. Anti-GLUT2, anti-CTLA-4 protein is injected as described above 2 hours prior to T-cell injection. A control group that received T-cells but is treated with a control antibody is also included to determine whether anti-CTLA-4 portion of control antibody can influence T-cell properties in vivo. As reported in the inventor's earlier study (Karumuthil-Melethil et al., 2010, *Journal of Immunology* 184:6695-708), adoptively transferred BDC2.5 TCR-Tg cells infiltrate the pancreas and destroy islets and induce hyperglycemia within 6-8 days. Therefore, one set of mice from each group is monitored for blood glucose levels every day for up to 10 days and every 3 days following that for 30 days to determine whether pathogenic properties of islet-infiltrating T-cells are suppressed in the anti-GLUT2, anti-CTLA-4 protein-injected mice. Upon anti-GLUT2, anti-CTLA-4 protein modulation of the pathogenic properties of islet infiltrating T-cells, the mice that received the protein then remain free of hyperglycemia for a longer period of time. A second set of mice is euthanized 96 hours post-cell transfer, immune cells isolated from pancreatic tissue, pancreatic lymph nodes and spleen are examined for Carboxyfluorescein succinimidyl ester (CFSE)$^+$ (/low) cells for proliferation profile, intracellular cytokines IL-10, IFN-gamma, IL-17, TGF-$\beta$1 levels, and expression of transcription factor Foxp3 by FACS. Upon anti-GLUT2, anti-CTLA-4 protein induction of T-cells with regulatory properties, BDC2.5 TCR-Tg T-cells recovered from this anti-GLUT2, anti-CTLA-4 protein treated mice then express Foxp3 and/or high levels of IL-10 or TGF-beta1.

A range of doses from 20 µg to 200 µg of anti-GLUT2, anti-CTLA-4 protein are tested for the treatment. Single or multiple injections of the anti-GLUT2, anti-CTLA-4 protein is used to suppress homogenous population of adoptively transferred pathogenic BDC2.5 T-cells. Multiple injections mitigate degradation of the anti-GLUT2, anti-CTLA-4 protein in vivo. Therefore, based on results from stability studies described above, experiments are repeated by daily injections with effective dose of the anti-GLUT2, anti-CTLA-4 protein for 3 days. In vitro activated T-cells of hyperglycemic NOD mice are injected to young NOD mice to advance hyperglycemia and study the effect of anti-GLUT2, anti-CTLA-4 protein treatment. This process mitigates $\beta$-cell destruction and hyperglycemia. Spleen cells from diabetic NOD mice are activated using immunodominant $\beta$-cell antigen peptides (such as: 1. Insulin B (9-23); 2. GAD65 (206-220); 3. GAD65 (524-543); 4. IA-2beta (755-777) and 5; IGRP (123-145) as described in the inventor's earlier study (Karumuthil-Melethil et al., 2010, *Journal of Immunology* 184:6695-708) before injecting into anti-GLUT2, anti-CTLA-4 protein recipient and control mice.

Example 9

Optimization of Anti-GLUT2, Anti-CTLA-4 Protein Treatment

Whether a single injection of the anti-GLUT2, anti-CTLA-4 protein is sufficient or intermittent injections are needed is determined using the protocol described below. Five mice are used per group to determine the minimum number of injections of the anti-GLUT2, anti-CTLA-4 protein needed to achieve effective protection. In one set of experiments, eight week old pre-diabetic NOD mice are injected intravenously with the anti-GLUT2-anti-CTLA-4 protein or control antibody either only once on day 1 or every other day (i.e. on days 1, 3, 5 and 7). In the second set of experiments, injections are repeated at two-week intervals. The effect of the anti-GLUT2, anti-CTLA-4 protein injection is assessed by weekly monitoring of blood glucose levels for up to 25 weeks Example 10

Determining the Efficacy of Anti-GLUT2, Anti-CTLA-4 Protein Treatment in Mice at Various Stages of Disease The experiments above indicated that anti-GLUT2, anti-CTLA-4 protein treatment can prevent the onset of Type 1 diabetes in NOD mice. However, whether anti-GLUT2, anti-CTLA-4 protein treatment can also stabilize glucose levels or reverse ongoing diabetes can be determined Groups of mice are treated at 8, 10, 12 weeks of age using an optimized anti-GLUT2, anti-CTLA-4 protein dose and disease progression monitored. In addition, pre-hyperglycemic mice (glucose levels between 150-250 mg/dl) and hyperglycemic mice (glucose levels >250 mg/dl) selected from mice of ages between 12 and 25 weeks are also treated with the optimized anti-GLUT2, anti-CTLA-4 protein dose and regimen. Prior to, and every 7 days after, the initiation of the treatment, the blood glucose levels are monitored in these mice for up to 25 weeks post-treatment. To ensure normal immune cell function and to avoid prolonged hyperglycemia-induced complications, diabetic test and control groups of mice are injected subcutaneously with insulin every day (2 U/mouse/day) for the first 30 days. This provides a sufficient period of time for the therapy to be effective under a euglycemic state and for the potential restoration of euglycemia under the condition of suppressed autoimmunity. It is anticipated that mice treated with the anti-GLUT2, anti-CTLA-4 protein would show significant delay in the onset of hyperglycemia when treated at pre-diabetic stage. Diabetic mice treated with this anti-GLUT2, anti-CTLA-4 protein may remain euglycemic even after withdrawing insulin treatment on day 30. Mice are continually treated bi-weekly with the anti-GLUT2, anti-CTLA-4 protein and determine blood glucose levels to determine the optimum amount of the protein that is used to keep the mice disease free. The optimum anti-GLUT2, anti-CTLA-4 protein treatment cannot protect mice beyond a certain point of disease progression if the treatment is stopped.

Example 11

Type 1 Diabetes Suppression by Anti-GLUT2, Anti-CTLA-4 Protein

Disease suppression can result from either direct suppression of effector T-cell (Teff) response due to CTLA-4 mediated down modulation or induction of Tregs, which in turn can suppress Teff cells. Based on the inventor's previous studies on CTLA-4 engagement studies (Karumuthil-Melethil et al., 2010, Id.; Li et al., 2007, Id.; Vasu et al., 2004, Id.; Perez et al., 2008, Id.), disease suppression is believed to involve both mechanisms of action. To investigate these mechanisms of action, T-cells from anti-GLUT2, anti-CTLA-4 protein-treated and control mice are examined for their phenotypic and functional properties. Eight week old mice are treated with an optimal dose of therapeutic anti-GLUT2, anti-CTLA-4 protein and control antibody twice at bi-weekly interval. Two weeks after the last injection mice are sacrificed; spleen and pancreatic draining lymph node cells from these mice are used for multiple immunological analyses. Pancreata are also isolated for histopathological studies.

Example 12

Analysis of Treg Frequency and Function

Figure 12:
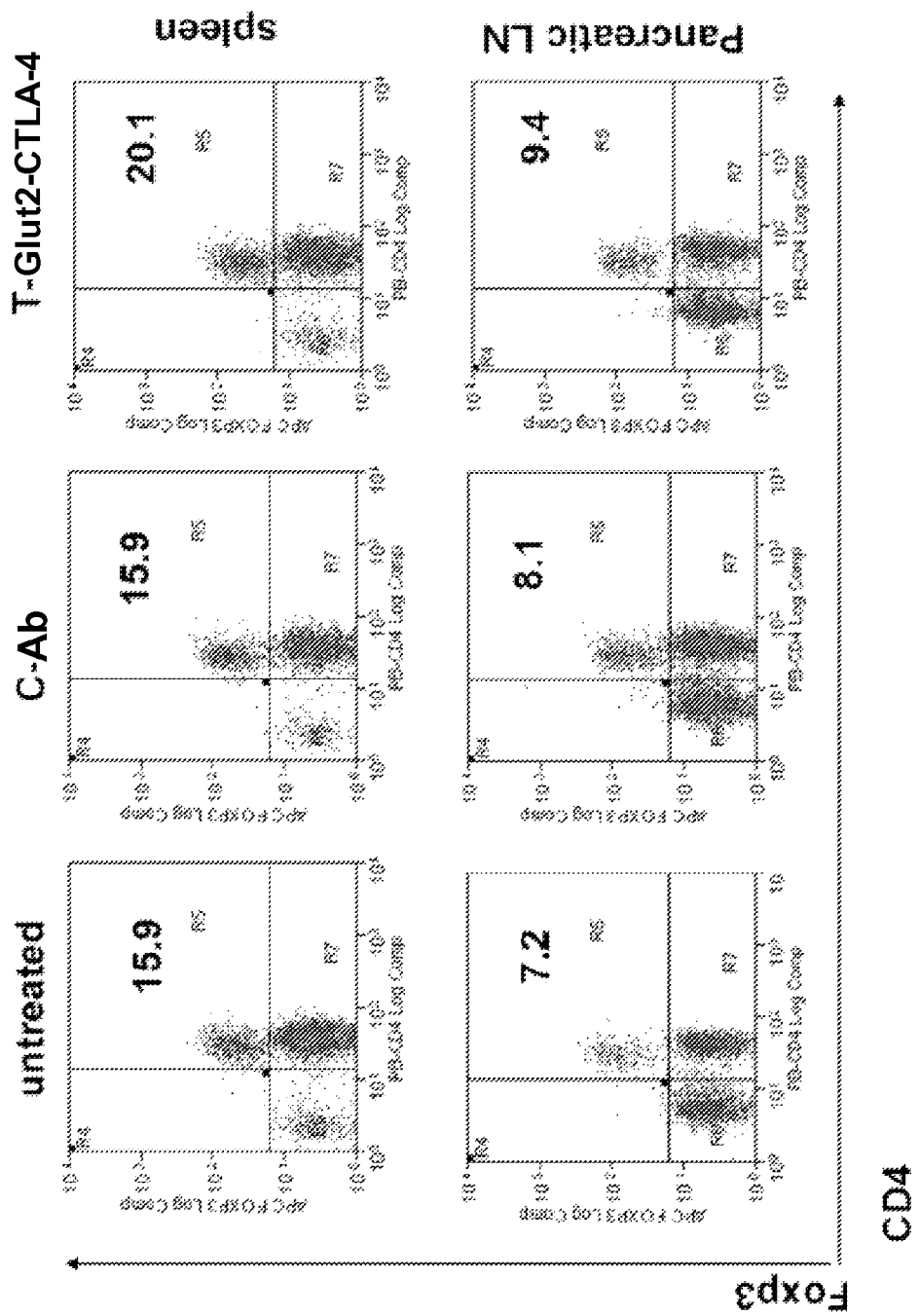
FIG. 12 shows FACS analysis showing increased Foxp3+ regulatory T cells in anti-GLUT2, anti-CTLA-4 protein-treated (T-Glut2-CTLA-4) NOD mice relative to mice that were left untreated or treated with a control antibody (C-Ab).

Foxp3 is a marker for Tregs and maintenance of its sustained expression determines the dominant suppressor function of Tregs (Williams & Rudensky, 2007, *Nature Immunology* 8:277-84; Wan & Flavell, 2007, *Nature* 445:766-70). Therefore, to determine the levels of induction of Tregs, cells from the spleen and pancreatic lymph nodes of mice that were repeatedly treated with anti-GLUT2, anti-CTLA-4 protein and control antibody at bi-weekly interval were analyzed by staining for intra-cellular Foxp3 expression. FACS analysis revealed increased Foxp3+ Treg percentages in anti-GLUT2, anti-CTLA-4 protein (T-Glut2-CTLA-4) treated mice compared to either untreated or control antibody (C-Ab) treated mice (FIG. 12).

IL-10 and TGF-beta have been implicated in the induction of Treg mediated tolerance. Therefore, to determine the levels of IL-10 production by Tregs, cells from the spleen and pancreatic lymph nodes of mice that were repeatedly treated with anti-GLUT2, anti-CTLA-4 protein and control antibody at bi-weekly interval were analyzed by staining for intra-cellular IL-10 expression. FACS analysis revealed increased CD4+ IL-10+ percentages in anti-GLUT2, anti-CTLA-4 protein treated mice than either untreated or control antibody treated mice.

Since a majority of T-cells with immunoregulatory properties express Foxp3, IL-10 and/or TGF-beta, expression levels of TGF-beta1 are also examined in these cells by FACS. Moreover, recently induced Tregs have been shown to express Glycoprotein A Repetitions Predominant (GARP) (Wang et al., 2008, *PLoS One* 3:e2705; Bhattacharya et al., 2011, *Journal of Leukocyte Biology* 89:235-49). Therefore, cells are stained for GARP as well as Foxp3 expression. These analyses indicate the proportion of induced versus natural Tregs and if the Tregs are increased in anti-GLUT2, anti-CTLA-4 protein treated mice relative to controls.

Figure 13:
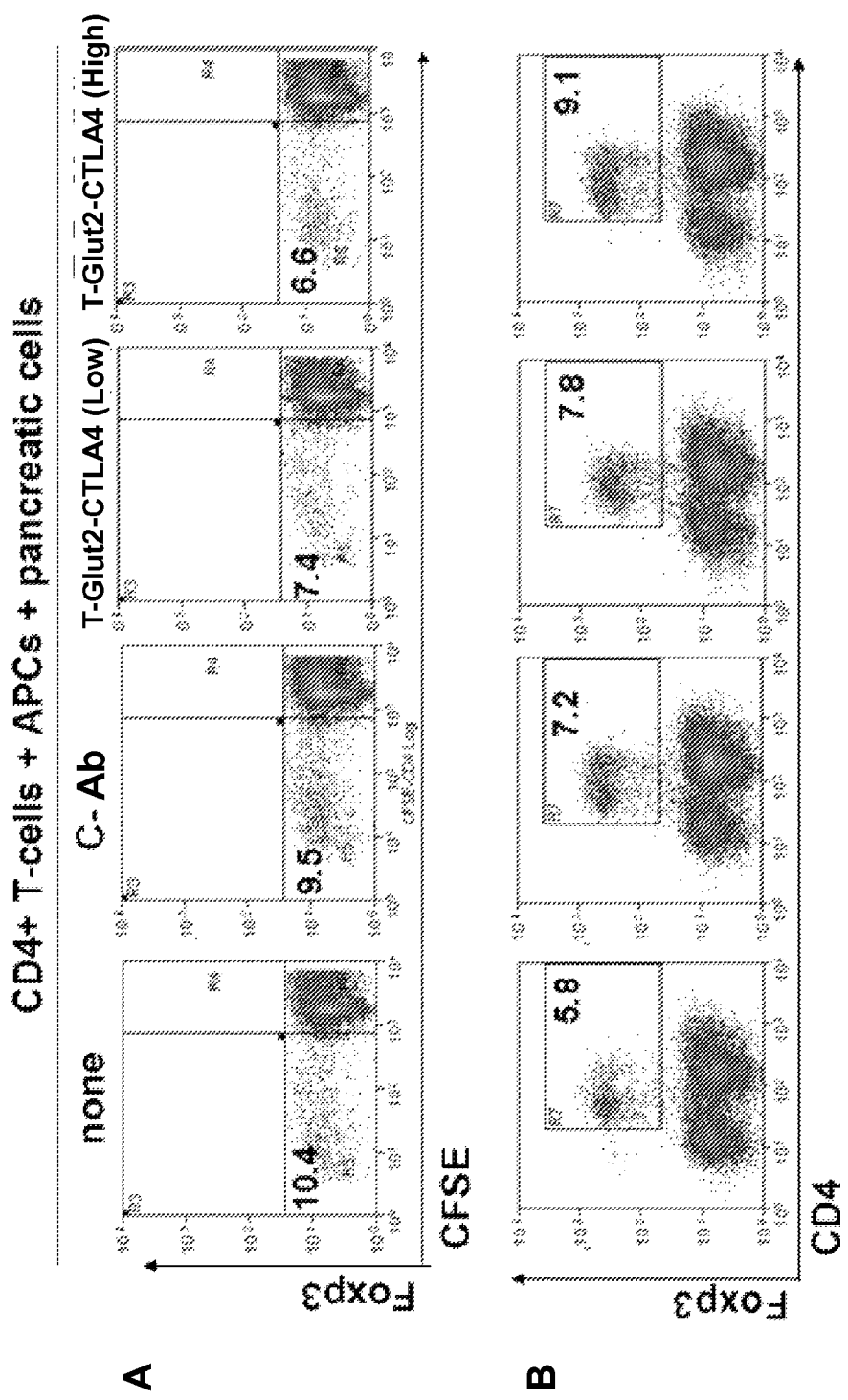
FIG. 13 shows FACS analysis showing reduced proliferation of effector T cells in response to pancreatic β-cell antigens in the presence of Tregs from anti-GLUT2, anti-CTLA-4 protein-treated NOD mice (T-Glut2-CTLA-4 (Low), T-Glut2-CTLA-4 (High)) relative to Tregs from untreated and C-Ab treated mice. The lower panel also shows increased Tregs in cultures of cells in vitro from T-Glut2-CTLA-4 treated NOD mice relative to the controls.
Figure 14:
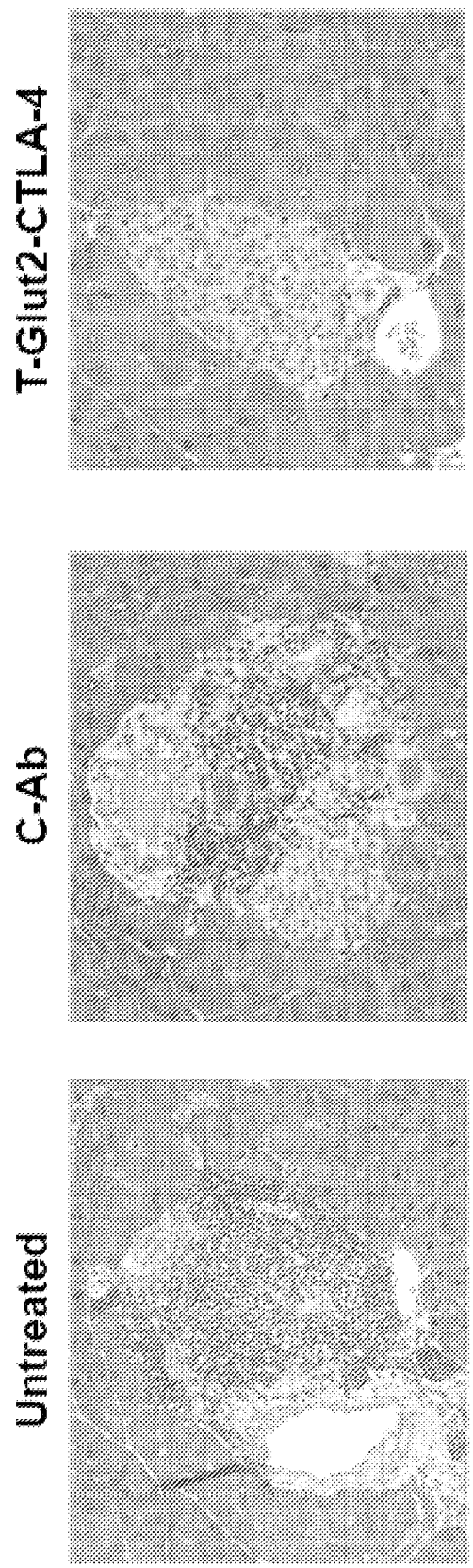
FIG. 14 shows hemtoxylin and eosin stained sections of pancreas from untreated, control Ab-treated and therapeutic T-Glut2-CTLA4 treated mice. Islets from untreated and control Ab treated mice show considerable lymphocytic infiltration, while the islet from T-Glut2-CTLA4 treated mice shows very little or no infiltration into the islet.

To examine the effects of anti-GLUT2, anti-CTLA-4 protein on T cell activation in vitro, splenic CD4+ T-cells were isolated from hyperglycemic NOD mice, labeled with CFSE and co-cultured with splenic APCs, immunodominant β-cell Ag peptides and total pancreatic cells in the absence or presence of different concentrations of anti-GLUT2, anti-CTLA-4 protein or control protein (C-Ab). Results showed suppression of CD4+ T-cell proliferation in the presence of anti-GLUT2, anti-CTLA-4 protein (T-Glut2-CTLA-4), but not the control antibody (C-Ab) (FIG. 13, upper panel). Additionally, after 96 hours of co-culture, an increase in the frequency of Foxp3+ Tregs in the anti-GLUT2, anti-CTLA-4 protein (T-Glut2-CTLA-4) treated cultures relative to the control (C-Ab) treated culture was noted (FIG. 13, lower panel).

If an increase in Treg frequency is observed, then the effector T-cell suppressive properties of CD4+CD25+ isolated from spleen and draining lymph node cells from anti-GLUT2, anti-CTLA-4 protein treated and control mice are compared. Effector CD4+CD25− T-cells from control and treated mice are labeled with CFSE and cultured either alone or in the presence of Tregs from control and anti-GLUT2, anti-CTLA-4 protein treated mice, and in the presence or absence of a mixture of immunodominant β-cell antigen peptides indicated above and splenic dendritic cells (DCs) as APCs (Karumuthil-Melethil et al., 2010, Id.). Alternatively, cells are stimulated using plate bound anti-CD3 Ab and soluble CD28 Ab. Cell proliferation is examined by CFSE dilution assay. The Tregs are cultured at different ratios of 1:1, 1:2, 1:4, 1:8, and 1:16 to evaluate their suppressive abilities. T-cells with regulatory properties induced by anti-GLUT2, anti-CTLA-4 protein can be Foxp3+ but produce IL-10 and/or TGF-beta1. Therefore, to compare the overall proliferative response of T-cells from treated and control mice, spleen and draining lymph node cells are labeled with CFSE, cultured in the presence of β-cell antigen peptides for 4 days, and proliferative response in CD4+ and CD8+ T-cells are examined by FACS.

Example 13

Cytokine Analyses

T-cells from spleen and pancreatic lymph nodes of anti-GLUT2, anti-CTLA-4 protein treated and untreated mice are isolated and cultured in the presence of β-cell antigen peptides or CD3/CD28 Abs as described above. Cultures are maintained for 3 days and the supernatants examined for cytokine levels. Pro-inflammatory and immunoregulatory cytokine levels are also measured in the serum samples collected from treated and untreated mice. Specifically levels of IL-2, IL-4, IL-6, IL-10, IL-12, IL-113, IFN-gamma, IL-17, TGF-beta and TNF-alpha are examined to differentiate between Th1, Th2 and regulatory T-cell responses. This serves as an indicator of the qualitative difference in the immune response between anti-GLUT2, anti-CTLA-4 protein treated and control mice.

Example 14

Histopathology of Islets

Histopathological examination of Hematoxylin and Eosin (H&E) stained sections of pancreatic tissue from different experimental groups of mice (from the 10-week treatment groups selected at random) revealed extensive lymphocytic infiltration of pancreatic tissue in untreated and control Ab treated mice. In contrast, lymphocytic infiltration was essentially absent in the pancreata of mice that were treated with therapeutic anti-GLUT2, anti-CTLA-4 protein (T-Glut2-CTLA4). These results show that T-Glut2-CTLA4 treatment resulted not only in the expansion of regulatory T-cells but that those cells were capable of suppressing β-cell specific immune response in vitro as well as in vivo.

Example 15

Generation of Recombinant Human GLUT2 and CTLA-4

Figure 15:
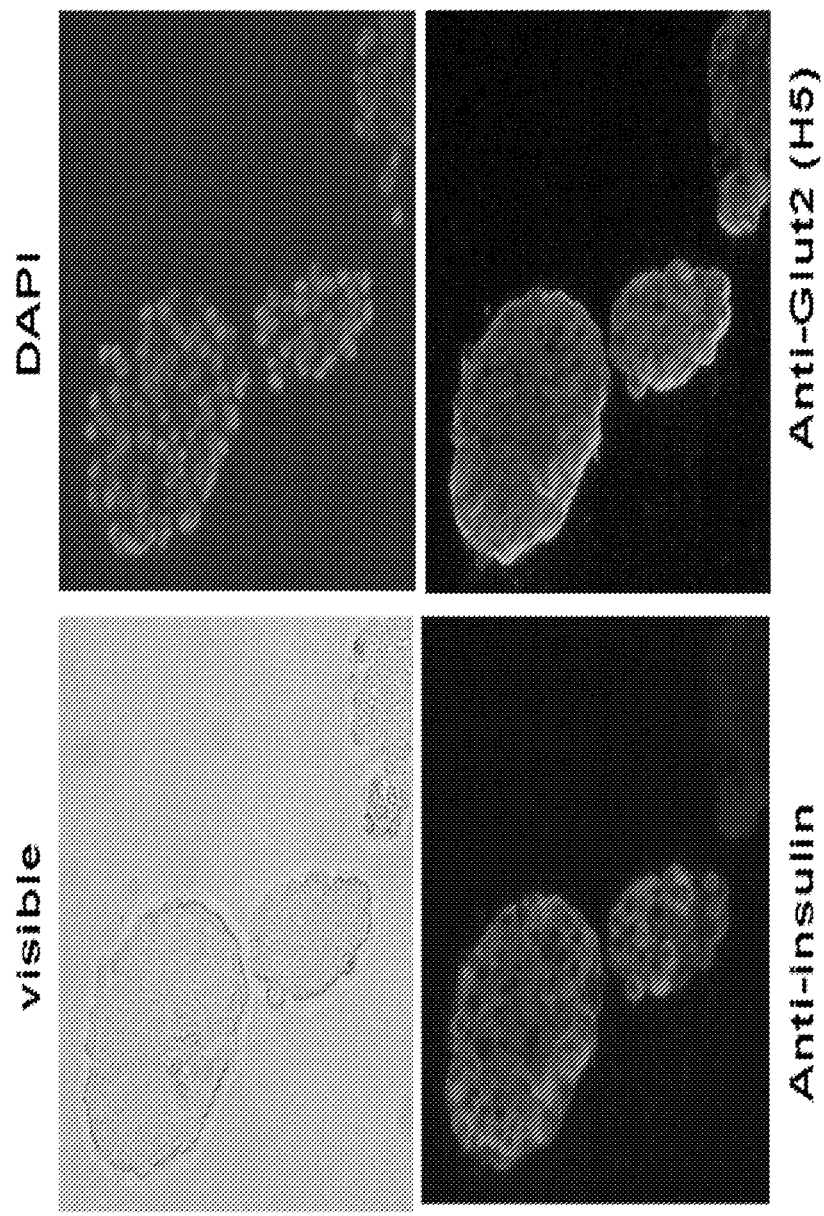
FIG. 15 shows that anti-mouse Glut2 mAb can recognize isolated human islets by immunofluorescence

Human and mouse GLUT2 share 81.87% identity at protein level, thus the inventors first verified if any of the functionally inert mAbs generated against mouse GLUT2 would also react to human GLUT2. The binding of the anti-GLUT2 mAbs to isolated human pancreatic islets obtained from The University of Illinois-Chicago's department of transplant surgery was tested by immunofluorescence. Anti-insulin antibody treatment of islets followed by staining with appropriate secondary reagents showed co-localization of anti-GLUT2 and anti-insulin antibodies on human pancreatic islets (FIG. 15). The specificity of its binding to human pancreatic β-cells by immunofluorescence following adsorption with GLUT2 and its functional inertness will be determined using isolated human islets. Thorough characterization of this mAb in recognizing human GLUT2 by Western Blot and FACS, will be achieved via expression of recombinant GLUT2 in mammalian cells. Like its mouse counterpart, human GLUT2 is a 524 amino acid transmemrane protein with a longest ectoplasmic domain of 67 amino acids. Expression and purification of both the hGLUT2-ectodomain and the full length hGLUT2 will be conducted as was done previously with mouse GLUT2. The plasmid pET15b will be used for expressing a 6×His-tagged ectodomain construct in *E. coli* cells, which will be purified by Ni++ affinity and reverse phase HPLC. The pcDNA-His plasmid will simultaneously be used to express the full length GLUT2 and purify using Ni++ affinity and reverse phase HPLC. To clone the Human GLUT2 cDNA, the primers 5'-GCGC CATATG AATGCACCTCAACAGG-TAATAATA-3' and 5'-GCGC GGATCC AAT GGACCA-GAGCATGGTGAT-3' were used to amplify ~200 bp cDNA construct using total RNA from HEK-293 cells cDNA for the ectodomain and cloned it in the pET15b vector. Likewise, a 1.5 kb full length GLUT2 cDNA was cloned using primers 5'-GCGC GGATCCACAGAAGATAAGGTCACTGGGAC-3' and 5'-GCGC GAATTC TTACACAGTCTCTGTAGCTC-CTAGG-3' and total RNA from HEK-293 cells into the pcDNA-His plasmid.

Human CTLA-4 is a 223 amino acid protein with an extracellular domain of 126 amino acids. Both the CTLA-4-extracellular domain and the CTLA-4 full length constructs will be purified in a manner similar to that used for GLUT2. The primer pair 5'-GCGC CATATG AAA GCA ATG CAC GTG GCC CAG-3' and 5'-GCGC GGATCC TTA AGA ATC TGG GCA CGG TTC-3' will be used for amplifying the cDNA encoding the extracellular domain. The primers 5'-GCGC GGATCC ATG GCT TGC CTT GGA TTT CAG-3' and 5'-GCGC GAATTC TCA ATT GAT GGG AAT AAA ATA-3' will be used for amplifying the full length cDNA. Total RNA from human peripheral blood mononuclear cells (PBMCs) will be used as template for the cDNA construction.

Example 16

Immunization of Mice with Recombinant Human GLUT2 and CTLA-4

The dose of immunization is expected to be the same as that which was used for mouse GLUT2. Thus 5 Balb/c mice per antigen group (for 2 groups, GLUT2 and CTLA-4) will be repeatedly immunized subcutaneously with 50 ug of purified Ecto-GLUT2 (or ecto-CTLA-4) emulsified in CFA and monitored for anti-Ecto-GLUT2 (or anti ecto-CTLA-4) antibody levels by ELISA using the recombinant proteins. When animals show high titers of antibodies (i.e. 1:100,000), they will be given a final intra venous dose of Ecto-GLUT2 (or ecto-CTLA-4) without the adjuvant and euthanized after 4 days. Splenocytes will be fused to SP2 myeloma cells and selected with HAT medium. Hybridoma supernatants will be tested for the presence of anti-GLUT2 (or anti-CTLA-4) antibodies by ELISA against Ecto-GLUT2 (or ecto-CTLA-4). Positive hybridomas will cloned and further screened for anti-GLUT2 IgG (or anti-CTLA-4 IgG) by western blot against FL-GLUT2 (or FL-CTLA-4).

Example 17

Screening and Characterization of the Anti-GLUT2 and Anti-CTLA-4 mAbs

Figure 16:
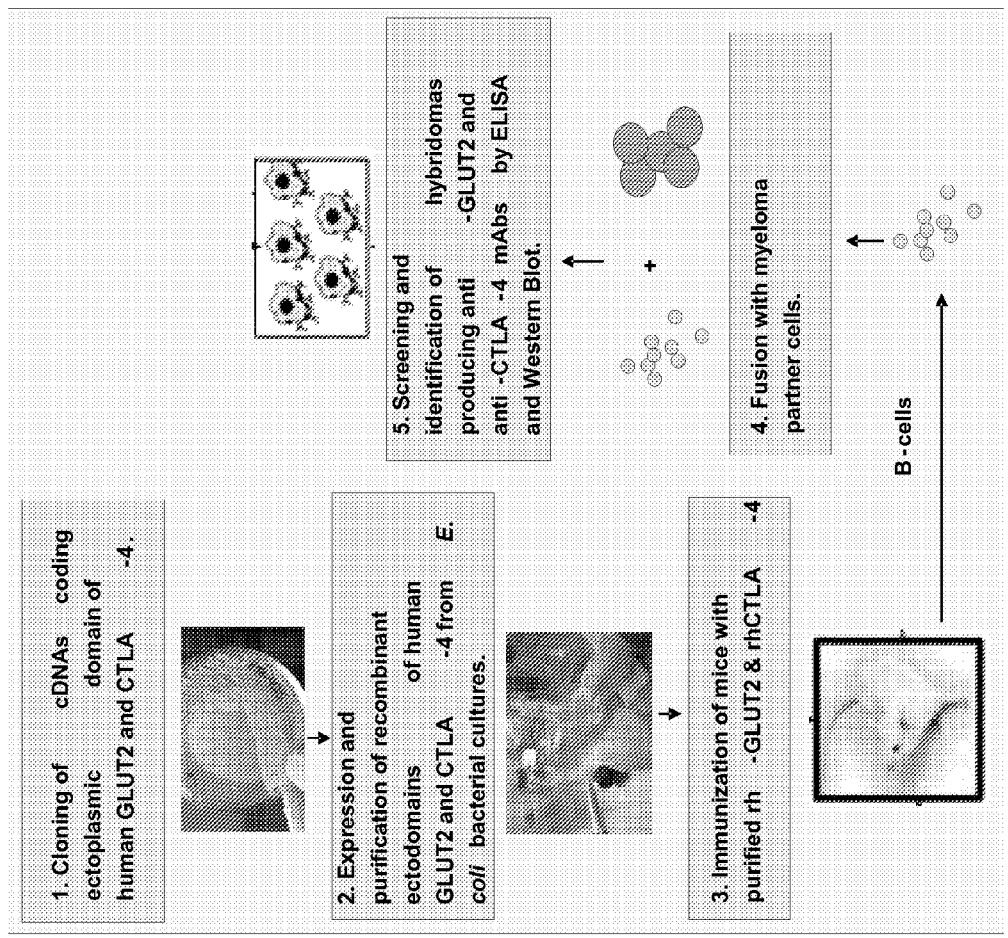
FIG. 16 shows the scheme for generating high specificity mAbs against human GLUT2 and CTLA-4.

The anti-GLUT2 and anti-CTLA-4 mAbs will be characterized first based on their high specificity for GLUT2 and CTLA4. The potential anti-GLUT2 mAb H5 described above will also be tested for its ability to specifically recognize recombinant and native human GLUT2. To do this we will express FL-GLUT2 and FL-CTLA-4 as recombinant constructs in HEK-293 cells. Since both are membrane bound proteins, they are expected to localize in the membrane of the 293 cells. These cells expressing GLUT2 or CTLA-4 will then be used to screen for mAb binding by immunofluorescence. Since these membrane-expressed proteins will likely be in their naturalistic conformation, this assay will be a more stringent test for high specificity mAbs than western blot (see FIG. 16 for the scheme).

mAbs will also be tested for their ability to recognize endogenous GLUT2 and CTLA-4 using cells that naturally express GLUT2 and CTLA-4, viz pancreatic islet cells and T-cells. The specific recognition of islet cells by anti-GLUT2 mAbs will then be analyzed by by immunofluorescence. Similarly the anti-CTLA-4 mAbs will be tested for specificity by analyzing their recognition of CTLA-4 on $CD4^+$ and $CD8^+$ T-cells present in human PBMCs by immunofluorescence.

To test if the anti-GLUT2 mAb binding interfered with GLUT2 function, human islet cells will be seeded in 96 well plates and incubated 0/N with media alone (control) or media plus different purified mAbs. Cells will then be washed in a modified Krebs-Ringer HEPES buffer (pH=7.4, 0.5% BSA) and insulin secretion will be stimulated using Krebs 2.8 mM glucose solution (basal) or 16.7 mM glucose solution for 1 h. The amount of insulin in the incubation buffers and cell extracts will be measured using an ultra sensitive insulin ELISA kit as we have done before. Insulin secretion will be expressed as a percentage of the total insulin, which is the sum of insulin in basal and stimulated buffers, and cell extracts. Systematic studies as described below using renal tubule, hepatocyte and intestinal epithelial cells will be used to rule out any off target effects of the anti-GLUT2 monoclonal antibodies. Only anti-GLUT2 mAbs which show non-interference with GLUT2 function will be chosen for humanization (see below).

Engagement of agonistic anti-CTLA-4 mAbs with CTLA-4 has been shown to inhibit IL-2 production and proliferation of primary $CD4^+$ T cells (39, 40). In contrast, inhibitory signal transduced by CTLA-4 engagement is known to increase IL-10 and TGF-β production (24). These tests will be used to functionally characterize the anti-CTLA-4 mAbs as agonistic, antagonistic or inert. $CD4^+$ cells will then be islolated from peripheral blood using appropriate cell isolation kits. In brief, blood samples will be drawn into heparinized tubes, diluted 1:1 with sterile HBSS (Ca++/Mg++ free) at room temperature and centrifuged on Ficoll-Paque gradients. Mononucleated cells (PBMCs) from the interface will be recovered, washed in HBSS, viability determined by trypan blue dye exclusion and used for the experiments. $CD4^+$ cells will be activated with anti-CD3/antiCD28 (in the presence or absence of antigen presenting cells) and incubated with or without anti-CTLA-4 mAbs (soluble or plate bound). Cell supernatant will be analyzed for IL-2, IL-10 and TGF-b levels by ELISA. Only agonistic mAbs will be selected for humanization, as described below.

Example 18

Construction of Human GLUT2 and CTLA-4 scFv cDNA

The example described below details the protocols used to clone and graft the mouse Ig CDR regions into human immunoglobulin heavy/light chain ScFv-Ig constructs and assemble them into a single coding framework for generating recombinant anti-GLUT2/anti-CTLA-4 bispecific ScFvs. Bispecific antibodies (BsAbs) are regarded as promising therapeutic agents due to their ability to simultaneously bind two different antigens. Several bispecific modalities have been developed, but their utility is limited due to problems with stability and manufacturing complexity. However, bispecific scFvIg proteins have the advantage of being a molecularly engineered homogeneous molecule with higher stability and feasible production. The inventors believe based on the results in mice described above, that targeting GLUT2 on human pancreas as well as CTLA-4 on human T cells with bi-specific scFvIg could be a potential therapy to treat autoimmune diabetes mellitus by suppressing pancreatic tissue antigen specific T cell activation through CTLA-4 engagement.

Hybridomas which are producing anti-human GLUT2 antibodies and those producing anti-human CTLA-4 will be used to amplify VL and VH sequences by RT-PCR (41, 42). Total RNA will be isolated with RNeasy plus mini kit (Qiagen). First strand will be synthesized using standard cDNA synthesis kits. The nucleotide sequences encoding VL and VH of murine antibody will be extracted from the Kabat's nucleotide data base (43) and subjected to the computer program FPAT (44) to analyze the presence of restriction enzyme recognition sites. Two sets of two primers each will be designed for the amplification of the VL and VH of anti-human GLUT2 and anti-human CTLA-4 murine monoclonal antibodies. VL-5' will be based on the N-terminal amino acid sequence of the light chain and contains 23 nucleotides encoding the N-terminal amino acids of the light chain and SfiI site 5' N-terminal to these nucleotides. VL-3' will be designed to have nucleotides complementary to those encoding a glycine and serine rich linker peptide (GGSSRSSSSGGGGSGGGG), and its 3' end complimentary to the joining (J) region of a mouse light chain. VH-5' will be designed to have nucleotides complementary to those encoding a glycine and serine rich linker peptide and 20 nucleotides encoding the N-terminal amino acids of the heavy chain. VH-3' will be designed to have a SfiI site with its 3' end complementary to the J region of the heavy chain (44). Two PCR reactions will be carried out to amplify VL and VH regions of each of GLUT2 and CTLA-4 antibodies from the corresponding hybridomas. The resulting VL and VH DNA fragments will be purified and used in overlapping PCR to produce the scFv antibody DNA linked by the glycine and serine linker for each of the GLUT2 and CTLA-4 (45).

Example 19

Screening for Properly Refolded GLUT2 and CTLA-4 scFv by Phage Display Screening In order to screen for properly refolded variable regions that are linked through the glycine and serine rich linker, a phage display screening will be used. Briefly, the GLUT2 and CTLA-4 scFv fragments will be purified and ligated into the SfiI sites of the phagemid pComb3H (46). The ligated DNA will be transformed into electro-competent E. coli XL1-Blue cells to obtain the phage library. Recombinant phages will be prepared from the library with the helper phage VCSM13 (46). The phage library obtained will be precipitated with polyethylene glycol and stored in Tris-buffered saline (TBS) containing 1% (w/v) bovine serum albumin (BSA) at 4° C. (45).

To enrich phages that display the scFv protein, the phage library will be bio-panned against recombinant human GLUT2 and human CTLA-4 proteins, a phage that displays properly refolded scFv that binds to GLUT2 or CTLA-4 respectively will remain bound to the plate bind while others will be removed by washing. The resulting bound phages will be grown in E. coli XL1-Blue with VCSM13, and the phage preparation will be obtained by polyethylene glycol precipitation. The phages will be panned a total of four times as described above. Fnal phage preparation will be used for screening individual clones. Phage eluted in the final step will be used to infect a suitable bacterial host, from which the phage DNA will be collected and the relevant scFv will be excised and sequenced to identify the candidate VL-VH sequence that can be used to construct bi-specific GLUT2-CTLA-4 scFvIg (ScFv-BsAb).

Example 20

Cloning, Expression and Purification of Mono-Specific and Bi-Specific Anti-GLUT2 and Anti-CTLA-4 scFvIg The candidate VL-VH sequences specific to human GLUT2 and CTLA-4 identified through phage display screening will be amplified by PCR and individually cloned into pCDM8-IgG1 mammalian expression plasmid vector. Briefly, the GLUT2 and CTLA-4 scFvs will be amplified using two primers. The forward primer is VL-5', which will be based on the N-terminal amino acid sequence of the light chain and contains 23 nucleotides encoding the N-terminal amino acids of the light chain and Sal I site 5' N-terminal to these nucleotides. The Reverse primer is VH-3', which will be designed to have a Bcl I site with its 3' end complementary to the J region of the heavy chain. The amplified scFvs using the previously described primers will be ligated into the pCDM8-IgG1 mammalian expression plasmid vector containing human IgG1 constant region sequences (47). GLUT2 IgG1 and CTLA-4 IgG1 fusion proteins will be produced by transient transfection of COS-7 cells with the monospecific expression plasmids and purified by Protein A-affinity chromatography as previously described (39, 42). At this stage we would have made humanized anti-GLUT2 and humanized anti-CTLA-4 ScFvs.

Figure 17:
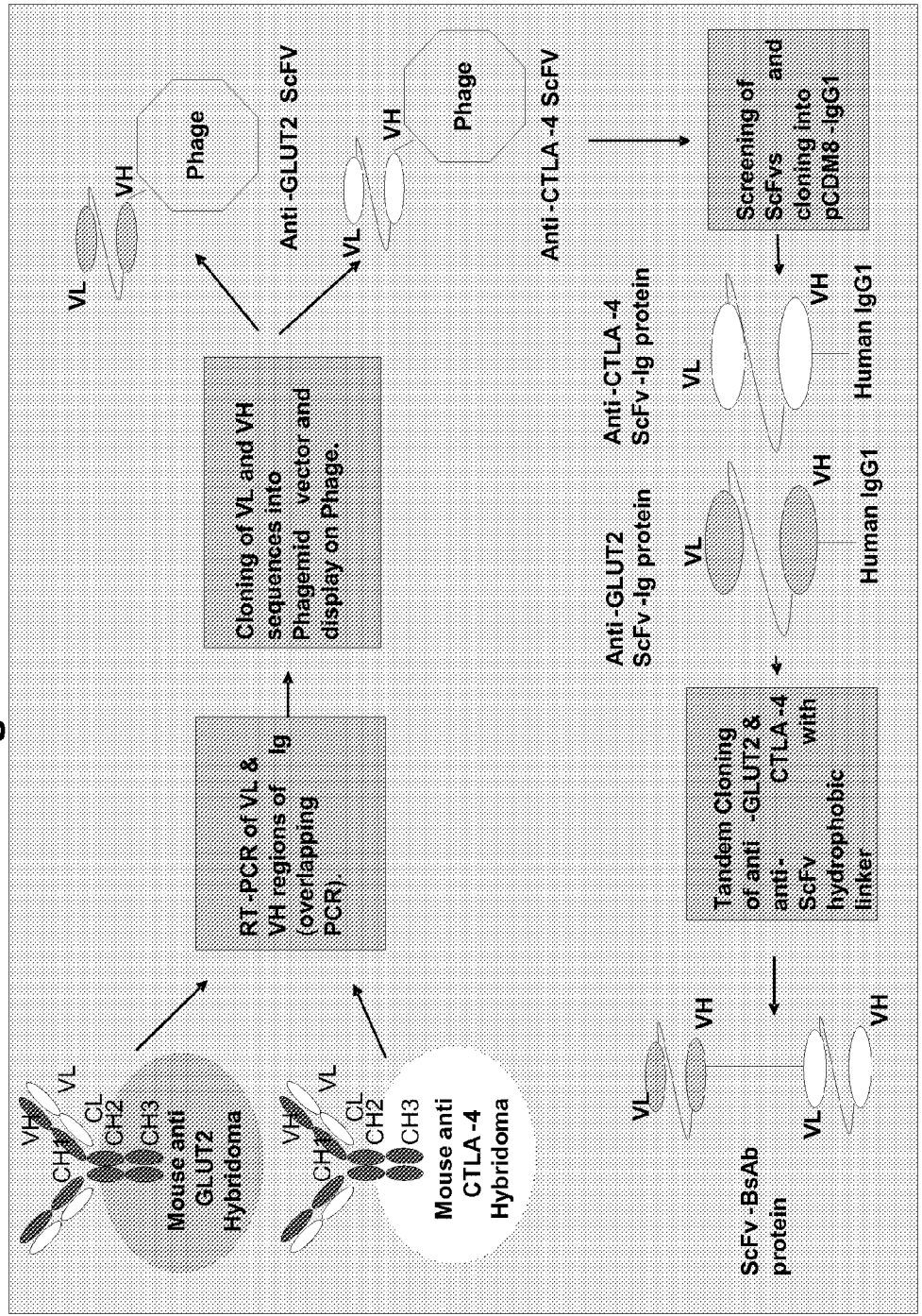
FIG. 17 shows the scheme for stepwise construction of anti-GLUT2/anti-CTLA-4 scFv-BsAb.

Purified monospecific anti-GLUT2 scFvIgG1 and anti-CTLA-4 scFvIgG1 will be tested for binding to human recombinant GLUT2 and CTLA-4 respectively by ELISA. Monoclonal antibodies to GLUT2 and CTLA-4 will be used as positive controls. The coding sequences for GLUT2 reactive scFvIgG1 will be amplified to generate a PCR product with a C-terminal hydrophobic linker using specific primers. Subsequently, a bi-specific scFvIgG1 will be created by cloning the GLUT2 scFv PCR product in frame into the anti-CTLA-4 scFvIgG1 expression vector. The bi-specific fusion protein will be produced by transient transfection of COS-7 cells with the bi-specific expression plasmid and purified using Protein A agarose beads as described previously (47). The bi-specific ScFv-BsAb protein will be tested for binding to recombinant human GLUT2 and CTLA-4 proteins by ELISA (see FIG. 17 for the scheme). The anti-GLUT2 and anti-CTLA-4 arms of the ScFv-BsAbs will also need to be verified for their functional properties. Thus, the anti-GLUT2 arm should be inert while the anti-CTLA-4 arm should be agonistic.

Chemically coupled bispecific humanized IgG4s can also be created. For this, PCR amplification of the variable regions of the heavy-chain (VH) and light-chains (VL) cDNAs will be performed using universal primers. The primers for the amplification of the VH cDNAs are: 5'-SARGTNMAGCTG-SAGTC-3' and 5'-AGGCTTACTAGT ACAATC- CCTGGGCACAAT-3' in which S=C, G; M=A, C; R=A, G; W=A, T. The primers for the amplification of the VLκ cDNAs are: 5'GAYATTGTMTSACMCARQCTMCA-3' and 5'-TAGAATTAACACTCATTCCTGTTGAA-3' in which Y=C, T. The primers for the amplification of the VLλ cDNAs are: 5'-CAGG CTGTTGTGACTCAGGAA-3' and 5'-CTTGGGCTGACCTAGGACAGT-3'. PCR products will be cloned into TOPO TA cloning vector (Invitrogen), amplified, and inserts sequenced to identify heavy & light chain CDR regions. The CDR regions will be further cloned into pFUSE-CHIg and pFUSE-CLIg and the plasmids will then be transfected into HEK 293 cells to generate stable cell lines that secrete humanized anti-GLUT2 and anti-CTLA-4 monoclonal antibody into the culture supernatant (48, 49). We will use the plasmids that code for the human IgG 4 frame-work (Fc) and scale up the cell culture and antibody purification studies to obtain mg quantities of each promising antibody. These two purified antibodies will then be chemically couples as described above.

Example 21

Assessment of β-Cell Targeting and Stability of BsAb Binding

The following protocols determine whether the recombinant anti-GLUT2/anti-CTLA-4 bispecific ScFv can effectively bind human pancreatic islets and downmodulate activated T-cell responses ex vivo.

While infiltrating T cells recognize β-cell specific antigens through TCR and migrate to islet of Langerhans in the pancreas, the BsAb is expected to bind to GLUT2 expressed on β-cells and engage CTLA-4 on infiltrating T cells. The inventors believe that by co-targeting CTLA-4 and GLUT2, the recombinant bispecific single-chain antibody will lead to suppression of effector T cell function and generation of β-cell specific Tregs which will inhibit the autoimmune effector T cells from destroying β-cells. Thus, the therapeutic efficacy of the ScFv-BsAb will depend on how efficiently it can bind to GLUT2 expressing β-cells. Therefore, the ScFv-BsAb will be tested for their ability to bind to GLUT2 on the surface on isolated human islets. BsAb binding will also be tested in vitro to other tissues that express GLUT2 and resultant pathology, if any. Next, this ScFv-BsAb will be examined for its ability to exert suppressive effect on activated T-cells co-cultured with isolated human islets. Activated T cells recovered from healthy human donors will be examined for changes in their phenotypic and functional properties. All experiments will be performed in triplicates and mean and standard deviation (SD) will be calculated. Standard statistical tools including student's t test will be applied and a P value of <0.05 will be considered significant. To determine if the BsAb can bind to β-cells in vitro, purified human BsAb will be tested for binding to isolated human islet by immunoflourescence. Anti-insulin staining will be used to determine co-localization of the BsAb and anti-insulin antibodies on pancreatic islets.

Next it will be determined if ScFv-BsAb has any adverse effects upon binding to GLUT2. GLUT2 is a bi-directional transporter and allows glucose to flow in two directions, which is required in liver cells to uptake and release glucose for glycolysis and during gluconeogenesis respectively. In pancreatic β-cells, it is required so that the intracellular environment can accurately gauge the serum glucose levels. All three monosaccharides are transported from the intestinal mucosal cell into the portal circulation by GLUT2 (50). Therefore, to the inventors will ensure that the anti-GLUT2 arm of the ScFv-BsAb will not adversely affect GLUT2 function. To test if ScFv-BsAb binding interferes with GLUT2 function, human islets will be obtained from Department of Transplant Surgery, University of Illinois-Chicago. Human islets will be seeded in 6-well plates. Cells will be treated with different doses of the ScFv-BsAb or control Ab for 24-48 hrs. Cells were then washed in a modified Krebs-Ringer HEPES buffer (pH=7.4, 0.5% BSA) and insulin secretion will be stimulated using Krebs 2.8 mM glucose solution (basal) or Krebs 16.7 mM glucose solution (stimulated) for 1 hr. Cells are then extracted with acid-ethanol for total insulin content measurement. The amount of insulin in the incubation buffers and cell extracts will be measured using an ultra sensitive mouse-insulin ELISA kit (Crystal Chem INC). Insulin secretion is expressed as a percentage of the total insulin content, which is the sum of insulin contained in basal and stimulated buffers and in cell extracts.

GLUT2 expression is not limited to beta cells and it is also expressed in liver, kidney and brain (51, 52). Independently of glucose metabolism, GLUT2 is believed to detect the presence of extracellular sugar and transduce signals to modulate cell functions, including beta-cell insulin secretion, renal re-absorption, and intestinal absorption according to the sugar environment (50). Thus, in order to ensure that the selected anti-GLUT2 mAb will not affect GLUT2 function in other tissues in which GLUT2 is expressed, systematic studies will be carried out. The off target effects of the anti-GLUT2 component of the ScFv-BsAb will be assessed using renal proximal tubule epithelial cells (RPTECs) (Lonza). RPTECs will be cultured in the presence of ScFv-BsAb, or control Ab for 24-48 hours. Since GLUT2 can modulate renal re-absorption, the following functional assays measuring glucose, phosphate and protein absorption will be conducted to determine if BsAb has any adverse effects on GLUT2 function in renal cells.

1) Glucose Uptake:

Glucose uptake is determined as described previously ((53). Briefly, 24-48 following treatment with ScFv-BsAb or control Ab, cells will be serum-starved, washed twice with Krebs-Ringer bicarbonate buffer containing 30 mM HEPES, pH 7.4, and 0.1% bovine seroalbumin (BSA) (Krebs-Ringer bicarbonate/HEPES [KRBH]/BSA) and incubated in KRBH/BSA for 30 min. Two wells per treatment are incubated in KRBH/BSA/0.4 mM Cytochalasin B (Sigma-Aldrich) to determine nonspecific glucose uptake. The assay will be initiated by addition of 2-deoxyglucose-D-[1-$^3$H] glucose (1 μCi per well; Amersham Biosciences) and 0.1 mM 2-deoxyglucose. The assay will be terminated after 10 min with phosphate buffered saline (PBS) containing 10 mM glucose and 0.2 mM cytochalasin B. Cells will be washed 3 times with ice-cold PBS/10 mM glucose. Cell lysates will be collected in 0.05 N NaOH/1% Triton X-100. Protein concentration will be determined by means of BCA protein assay (Pierce). Cell-associated radioactivity (disintegrations per minute) will be normalized to the protein concentration. If it is found that a given ScFv-BsAb can affect glucose uptake then it would indicate that it is not suitable for therapeutic use.

2) Sodium-Dependent Phosphate Uptake:

Sodium-dependent phosphate uptake assay will be performed as described previously (54). In brief, cells will be rinsed three times with uptake buffer consisting of (mM) 137 NaCl, 5.4 KCl, 2.8 CaCl2, 1.2 MgSO4, and 1 KH2PO4 or a buffer in which sodium chloride was replaced by 137 mM choline chloride. For uptake, sodium chloride- or choline chloride-containing buffer will be supplemented with 1 uCi of [32-P]phosphoric acid per well. Uptake is allowed for 1 or 10 min at RT. Thereafter, cells will be washed three times with ice-cold choline chloride buffer and lysed for 30 min with 0.5 M NaOH. Two hundred microliters of lysate per well will be assayed for total radioactivity on a Packard 1900CA TRI-CARB (Packard Instrument, Sterling, Va.) liquid scintillation analyzer. If it is found that a given ScFv-BsAb can affect phosphate uptake then it would indicate that it is not suitable for therapeutic use.

3) Protein Uptake:

Cell culture-grade bovine aprotinin (Sigma) will be labeled with Alexa Fluor 633 succinimidyl ester (Molecular Probes, Invitrogen, Eugene, Oreg.) according to manufacturer's instructions. Unincorporated dye is removed with a 1-kDa-cutoff minidialysis kit (Amersham Biosciences, Piscataway, N.J.) according to manufacturer's instructions at 4° C. overnight. Uptake will be analyzed as described previously (55). In brief, cells will be starved for 24 h in DMEM-Ham's F-12-4 mM L-glutamine. Labeled aprotinin is diluted to final concentrations in PBS containing Ca2+/Mg2+, and cells will be incubated for 30 min at 37° C. or 4° C. Thereafter, cells will be put on ice and rinsed seven times with ice-cold PBS, and protein uptake will be determined on a FACS Calibur. If it is found that a given ScFv-BsAb can affect protein uptake then it would indicate that it is not suitable for therapeutic use.

Example 22

Determination of Whether ScFv-BsAb can Exert Suppressive Effect on Activated T-Cells In the experiments previously conducted with chemically coupled BsAbs, the frequency of Tregs was analyzed in the spleen and pancreatic lymph nodes of mice treated with C-BsAb and T-BsAb. An increase in Foxp3+ Tregs in T-BsAb treated mice was observed (20.1% and 9.4% in spleen and pancreatic LN respectively) relative to both untreated and C-BsAb treated mice (15.9%, and 7.2 and 8.1% respectively) (FIG. 12). To further examine the effects of BsAb on T cell activation in vitro, we isolated splenic $CD4^+$ T-cells from hyperglycemic NOD mice, labeled them with CFSE and co-cultured them with splenic APCs, immunodominant β-cell Ag peptides and total pancreatic cells in the absence or presence of different concentrations of T-BsAb or C-BsAb. T-BsAb was expected to tether to the pancreatic β-cell through GLUT2 and interact with CTLA-4 expressed on β-cells recognizing activated $CD4^+$ T-cells and suppress T cell activation relative to C-BsAb coated cells. Results showed suppression of $CD4^+$ T-cell proliferation in the presence of T-BsAb (6.6% versus 10.4 in controls) but not C-BsAb (9.5 versus 10.4%) (FIG. 13, upper panel). Additionally, after 96-hours of co-culture, we noticed an increase in the frequency of Tregs in the T-BsAb treated cultures (9.1% versus 5.8%) relative to the C-BsAb treated cultures (Fid-13 lower panel).

Similarly, to measure the ability of the ScFv-BsAb to prevent cell-induced T cell activation (56), PBMCs will be isolated from donor blood samples. FACS sorted $CD4^+$ T cells will be activated with anti-CD3/anti-CD28 for 24 hrs. Alternatively, PBMCs themselves may be cultured in complete medium in the presence of phytohemaglutinin A (PHA) at a final concentration of 2 ng/ml for 48 hours at 37° C. and $CD4^+$ cells sorted post-activation. Activated $CD4^+$ T cells will then be CSFE-labeled and co-cultured with islolated human islets in the presence of ScFv-BsAb, control Ab or media alone. Five days following treatment, $CD4^+$ T cells will be analyzed by FACS. Specifically we will look for inhibition of proliferation of $CD4^+CD25^-$ effector T cells (Teff), and expansion/induction of $CD4^+CD25^{high}Foxp3^+$ regulatory T cells (Tregs). Additionally, intracellular cytokines IL-2, IL-10, IFN-γ, IL-17, TGF-β1 levels will be determined by FACS while cytokine release in the media supernatants will be analyzed by ELISA.

To examine if the suppression of $CD4^+$ T cell proliferation is due to increased numbers of Tregs their frequency will be determined in cultures containing $CD4^+$ T cells and ScFv-BsAb coated β-cells, relative to cultures containing control Ab coated β-cells. If suppression of T cell proliferation with a concomitant increase in Tregs (i.e. Foxp3+ cells) is found in cultures containing ScFv-BsAb coated β-cells, and if this suppression is reversed upon addition of antibodies to TGF-β and/or IL-10 then it would strongly suggest a role for Tregs in immune suppression, perhaps through increased production of suppressor cytokines such as TGF-β and IL-10. If the suppression is not reversed in the presence of antibodies to TGF-β and/or IL-10 then it would suggest that the T-BsAb can directly down modulate T cell responses through CTLA-4 mediated signaling such as suppression of IL-2 production. It is now evident that $CD8^+$ T cells are also involved in disease pathogenesis in T1D. Various adoptive transfer studies in NOD mice support the importance of both $CD4^+$ and $CD8^+$ T cell subpopulations in diabetogenesis. It will be determined if the disclosed ScFv-BsAb has the potential to mediate its therapeutic effect also by suppressing $CD8^+$ T cell function through ex vivo studies. To test if the ScFv-BsAb can down modulate $CD8^+$ T-cell mediated effects on pancreatic β-cells, $CD8^+$ T-cells from anti-CD3 (or PHA) activated PBMCs isolated from diabetic donors will be sorted for, labeled with CFSE and co-cultured in the presence of pancreatic islet cells for 72 hours. These cultures will be left untreated or treated with the ScFv-BsAb or Control Ab. $CD8^+$ T-cell proliferation by CFSE dilution and the extent of CTL activity will be determined by measuring Granzyme-B release by ELISA. This will reveal if ScFv-BsAb can suppress $CD8^+$ T-cell responses. The protocols described above can also be conducted using hepatocytes and intestinal epithelial cells.

It should be understood that the foregoing disclosure emphasizes certain specific embodiments of the invention and that all modifications or alternatives equivalent thereto are within the spirit and scope of the invention as set forth in the appended claims.

REFERENCES

1. Yoon J W, Jun H S. 2001. Cellular and molecular pathogenic mechanisms of insulin-dependent diabetes mellitus. *Ann NY Acad Sci* 928: 200-11
2. Kukreja A, Cost G, Marker J, Zhang C, Sun Z, Lin-Su K, Ten S, Sanz M, Exley M, Wilson B, Porcelli S, Maclaren N. 2002. Multiple immuno-regulatory defects in type-1 diabetes. *J Clin Invest* 109: 131-40
3. Skarsvik S, Tiittanen M, Lindstrom A, Casas R, Ludvigsson J, Vaarala O. 2004. Poor in vitro maturation and pro-inflammatory cytokine response of dendritic cells in children at genetic risk of type 1 diabetes. *Scand J Immunol* 60: 647-52
4. Bluestone J A. 1997. Is CTLA-4 a master switch for peripheral T cell tolerance? *J Immunol* 158: 1989-93
5. Lindley S, Dayan C M, Bishop A, Roep B O, Peakman M, Tree T I. 2005. Defective suppressor function in CD4(+) CD25(+) T-cells from patients with type 1 diabetes. *Diabetes* 54: 92-9
6. Alard P, Manirarora J N, Parnell S A, Hudkins J L, Clark S L, Kosiewicz M M. 2006. Deficiency in NOD antigen-presenting cell function may be responsible for suboptimal CD4+CD25+ T-cell-mediated regulation and type 1 diabetes development in NOD mice. *Diabetes* 55: 2098-105
7. Araki M, Chung D, Liu S, Rainbow D B, Chamberlain G, Garner V, Hunter K M, Vijayakrishnan L, Peterson L B, Oukka M, Sharpe A H, Sobel R, Kuchroo V K, Wicker L S. 2009. Genetic evidence that the differential expression of the ligand-independent isoform of CTLA-4 is the molecular basis of the Idd5.1 type 1 diabetes region in nonobese diabetic mice. *J Immunol* 183: 5146-57
8. Yadav D, Hill N, Yagita H, Azuma M, Sarvetnick N. 2009. Altered availability of PD-1/PD ligands is associated with the failure to control autoimmunity in NOD mice. *Cell Immunol* 258: 161-71
9. Linsley P S, Greene J L, Brady W, Bajorath J, Ledbetter J A, Peach R. 1994. Human B7-1 (CD80) and B7-2 (CD86) bind with similar avidities but distinct kinetics to CD28 and CTLA-4 receptors. *Immunity* 1: 793-801
10. Tivol E A, Borriello F, Schweitzer A N, Lynch W P, Bluestone J A, Sharpe A H. 1995. Loss of CTLA-4 leads to massive lymphoproliferation and fatal multiorgan tissue destruction, revealing a critical negative regulatory role of CTLA-4. *Immunity* 3: 541-7
11. Saverino D, Merlo A, Bruno S, Pistoia V, Grossi C E, Ciccone E. 2002. Dual effect of CD85/leukocyte Ig-like receptor-lag-like transcript 2 and CD152 (CTLA-4) on cytokine production by antigen-stimulated human T cells. *J Immunol* 168: 207-15
12. Karumuthil-Melethil S, Perez N, Li R, Prabhakar B S, Holterman M J, Vasu C. 2010. Dendritic cell-directed CTLA-4 engagement during pancreatic beta cell antigen presentation delays type 1 diabetes. *J Immunol* 184: 6695-708
13. Li R, Perez N, Karumuthil-Melethil S, Prabhakar B S, Holterman M J, Vasu C. 2007. Enhanced engagement of CTLA-4 induces antigen-specific CD4+CD25+Foxp3+ and CD4+CD25− TGF-beta1+ adaptive regulatory T cells. *J Immunol* 179: 5191-203
14. Vasu C, Prabhakar B S, Holterman M J. 2004. Targeted CTLA-4 engagement induces CD4+CD25+CTLA-4-high T regulatory cells with target (allo)antigen specificity. *J Immunol* 173: 2866-76
15. Vasu C, Gorla S R, Prabhakar B S, Holterman M J. 2003. Targeted engagement of CTLA-4 prevents autoimmune thyroiditis. *Int Immunol* 15: 641-54
16. Perez N, Karumuthil-Melethil S, Li R, Prabhakar B S, Holterman M J, Vasu C. 2008. Preferential costimulation by CD80 results in IL-10-dependent TGF-beta1(+)-adaptive regulatory T cell generation. *J Immunol* 180: 6566-76
17. Rao S, Vasu C, Martinez O, Kaithamana S, Prabhakar B S, Holterman M J. 2001. Targeted delivery of anti-CTLA-4 antibody downregulates T cell function in vitro and in vivo. *Clin Immunol* 101: 136-45
18. Cernea S, Pozzilli P. 2008. New potential treatments for protection of pancreatic B-cell function in Type 1 diabetes. *Diabet Med* 25: 1259-67
19. Atkinson M A, Eisenbarth G S. 2001. Type 1 diabetes: new perspectives on disease pathogenesis and treatment. *Lancet* 358: 221-9
20. Todd J A, Wicker L S. 2001. Genetic protection from the inflammatory disease type 1 diabetes in humans and animal models. *Immunity* 15: 387-95
21. Chatenoud L. 2003. CD3-specific antibody-induced active tolerance: from bench to bedside. *Nature reviews. Immunology* 3: 123-32
22. Chung D T, Korn T, Richard J, Ruzek M, Kohm A P, Miller S, Nahill S, Oukka M. 2007. Anti-thymocyte globulin (ATG) prevents autoimmune encephalomyelitis by expanding myelin antigen-specific Foxp3+ regulatory T cells. *International immunology* 19: 1003-10
23. Londrigan S L, Sutherland R M, Brady J L, Carrington E M, Cowan P J, d'Apice A J, O'Connell P J, Zhan Y, Lew A M. 2010. In situ protection against islet allograft rejection by CTLA4Ig transduction. *Transplantation* 90: 951-7
24. Vergani A, D'Addio F, Jurewicz M, Petrelli A, Watanabe T, Liu K, Law K, Schuetz C, Carvello M, Orsenigo E, Deng S, Rodig S J, Ansari J M, Staudacher C, Abdi R, Williams J, Markmann J, Atkinson M, Sayegh M H, Fiorina P. 2010. A novel clinically relevant strategy to abrogate autoimmunity and regulate alloimmunity in NOD mice. *Diabetes* 59: 2253-64
25. Sharpe A H, Freeman G J. 2002. The B7-CD28 superfamily. *Nat Rev Immunol* 2: 116-26
26. Thorens B, Roduit R. 1994. Regulated expression of GLUT2 in diabetes studied in transplanted pancreatic beta cells. *Biochem Soc Trans* 22: 684-7
27. Tang Q, Adams J Y, Penaranda C, Melli K, Piaggio E, Sgouroudis E, Piccirillo C A, Salomon B L, Bluestone J A. 2008. Central role of defective interleukin-2 production in the triggering of islet autoimmune destruction. *Immunity* 28: 687-97
28. Trembleau S, Penna G, Bosi E, Mortara A, Gately M K, Adorini L. 1995. Interleukin 12 administration induces T helper type 1 cells and accelerates autoimmune diabetes in NOD mice. *J Exp Med* 181: 817-21
29. Chen Z, Herman A E, Matos M, Mathis D, Benoist C. 2005. Where CD4+CD25+ T reg cells impinge on autoimmune diabetes. *J Exp Med* 202: 1387-97
30. Cheatem D, Ganesh B B, Gangi E, Vasu C, Prabhakar B S. 2009. Modulation of dendritic cells using granulocyte-macrophage colony-stimulating factor (GM-CSF) delays type 1 diabetes by enhancing CD4+CD25+ regulatory T cell function. *Clin Immunol* 131: 260-70
31. Gaudreau S, Guindi C, Menard M, Besin G, Dupuis G, Amrani A. 2007. Granulocyte-macrophage colony-stimulating factor prevents diabetes development in NOD mice by inducing tolerogenic dendritic cells that sustain the suppressive function of CD4+CD25+ regulatory T cells. *J Immunol* 179: 3638-47
32. O'Shea J J, Ma A, Lipsky P. 2002. Cytokines and autoimmunity. *Nature reviews. Immunology* 2: 37-45
33. Silva L C, Ortigosa L C, Benard G. 2010. Anti-TNF-alpha agents in the treatment of immune-mediated inflammatory diseases: mechanisms of action and pitfalls. *Immunotherapy* 2: 817-33
34. Shrikant P, Khoruts A, Mescher M F. 1999. CTLA-4 blockade reverses CD8+ T cell tolerance to tumor by a CD4+ T cell- and IL-2-dependent mechanism. *Immunity* 11: 483-93

35. Ratts R B, Arredondo L R, Bittner P, Perrin P J, Lovett-Racke A E, Racke M K. 1999. The role of CTLA-4 in tolerance induction and ttigen administration cell differentiation in experimental autoimmune encephalomyelitis: i.v. antigen administration. *Int Immunol* 11: 1889-96
36. Schwarz A, Beissert S, Grosse-Heitmeyer K, Gunzer M, Bluestone J A, Grabbe S, Schwarz T. 2000. Evidence for functional relevance of CTLA-4 in ultraviolet-radiation-induced tolerance. *J Immunol* 165: 1824-31
37. Chai J G, Vendetti S, Amofah E, Dyson J, Lechler R. 2000. CD152 ligation by CD80 on T cells is required for the induction of unresponsiveness by costimulation-deficient antigen presentation. *J Immunol* 165: 3037-42
38. Fife B T, Griffin M D, Abbas A K, Locksley R M, Bluestone J A. 2006 Inhibition of T cell activation and autoimmune diabetes using a B cell surface-linked CTLA-4 agonist. *J Clin Invest* 116: 2252-61
39. Glinka Y, Chang Y, Prud'homme G J. 2006. Protective regulatory T cell generation in autoimmune diabetes by DNA covaccination with islet antigens and a selective CTLA-4 ligand. *Mol Ther* 14: 578-87
40. Fife B T, Griffin M D, Abbas A K, Locksley R M, Bluestone J A. 2006 Inhibition of T cell activation and autoimmune diabetes using a B cell surface-linked CTLA-4 agonist. *The Journal of clinical investigation* 116: 2252-61
41. Karumuthil-Melethil S, Perez N, Li R, Prabhakar B S, Holterman M J, Vasu C. 2010. Dendritic cell-directed CTLA-4 engagement during pancreatic beta cell antigen presentation delays type 1 diabetes. *Journal of immunology* 184: 6695-708
42. Mabry R, Snavely M. 2010. Therapeutic bispecific antibodies: The selection of stable single-chain fragments to overcome engineering obstacles. *IDrugs* 13: 543-9
43. Hayden M S, Linsley P S, Gayle M A, Bajorath J, Brady W A, Norris N A, Fell H P, Ledbetter J A, Gilliland L K. 1994. Single-chain mono- and bispecific antibody derivatives with novel biological properties and antitumour activity from a COS cell transient expression system. *Ther Immunol* 1: 3-15
44. Dreier T, Lorenczewski G, Brandl C, Hoffmann P, Syring U, Hanakam F, Kufer P, Riethmuller G, Bargou R, Baeuerle P A. 2002. Extremely potent, rapid and costimulation-independent cytotoxic T-cell response against lymphoma cells catalyzed by a single-chain bispecific antibody. *Int J Cancer* 100: 690-7
45. Offner S, Hofineister R, Romaniuk A, Kufer P, Baeuerle P A. 2006. Induction of regular cytolytic T cell synapses by bispecific single-chain antibody constructs on MHC class I-negative tumor cells. *Mol Immunol* 43: 763-71
46. May K F, Jr., Roychowdhury S, Bhatt D, Kocak E, Bai X F, Liu J Q, Ferketich A K, Martin E W, Jr., Caligiuri M A, Zheng P, Liu Y. 2005. Anti-human CTLA-4 monoclonal antibody promotes T-cell expansion and immunity in a hu-PBL-SCID model: a new method for preclinical screening of costimulatory monoclonal antibodies. *Blood* 105: 1114-20
47. Brunner M C, Chambers C A, Chan F K, Hanke J, Winoto A, Allison J P. 1999. CTLA-4-Mediated inhibition of early events of T cell proliferation. *J Immunol* 162: 5813-20
48. Blair P J, Riley J L, Levine B L, Lee K P, Craighead N, Francomano T, Perfetto S J, Gray G S, Carreno B M, June C H. 1998. CTLA-4 ligation delivers a unique signal to resting human CD4 T cells that inhibits interleukin-2 secretion but allows Bcl-X(L) induction. *J Immunol* 160: 12-5
49. Bradbury A, Cattaneo A. 1995. The use of phage display in neurobiology. *Trends Neurosci* 18: 243-9
50. Gilliland L K, Norris N A, Marquardt H, Tsu T T, Hayden M S, Neubauer M G, Yelton D E, Mittler R S, Ledbetter J A. 1996. Rapid and reliable cloning of antibody variable regions and generation of recombinant single chain antibody fragments. *Tissue Antigens* 47: 1-20
51. Chen H T, Kabat E A, Lundblad A, Ratcliffe R M. 1987. Nucleotide and translated amino acid sequences of cDNA coding for the variable regions of the light and heavy chains of mouse hybridoma antibodies to blood group A and B substances. *J Biol Chem* 262: 13579-83
52. Chaudhary V K, Batra J K, Gallo M G, Willingham M C, FitzGerald D J, Pastan I. 1990. A rapid method of cloning functional variable-region antibody genes in *Escherichia coli* as single-chain immunotoxins. *Proc Natl Acad Sci USA* 87: 1066-70
53. Hussein A H, Davis E M, Halperin S A, Lee S F. 2007. Construction and characterization of single-chain variable fragment antibodies directed against the *Bordetella pertussis* surface adhesins filamentous hemagglutinin and pertactin. *Infect Immun* 75: 5476-82
54. Manosroi J, Tayapiwatana C, Gotz F, Werner R G, Manosroi A. 2001. Secretion of active recombinant human tissue plasminogen activator derivatives in *Escherichia coli*. *Appl Environ Microbiol* 67: 2657-64
55. Connelly R J, Hayden M S, Scholler J K, Tsu T T, Dupont B, Ledbetter J A, Kanner S B. 1998. Mitogenic properties of a bispecific single-chain Fv-Ig fusion generated from CD2-specific mAb to distinct epitopes. *Int Immunol* 10: 1863-72
56. Jones P T, Dear P H, Foote J, Neuberger M S, Winter G. 1986. Replacing the complementarity-determining regions in a human antibody with those from a mouse. *Nature* 321: 522-5
57. Tempest P R, Bremner P, Lambert M, Taylor G, Furze J M, Carr F J, Harris W J. 1991. Reshaping a human monoclonal antibody to inhibit human respiratory syncytial virus infection in vivo. *Biotechnology* (NY) 9: 266-71
58. Leturque A, Brot-Laroche E, Le Gall M. 2009. GLUT2 mutations, translocation, and receptor function in diet sugar managing. *Am J Physiol Endocrinol Metab* 296: E985-92
59. Thorens B, Wu Y J, Leahy J L, Weir G C. 1992. The loss of GLUT2 expression by glucose-unresponsive beta cells of db/db mice is reversible and is induced by the diabetic environment. *J Clin Invest* 90: 77-85
60. Garcia M A, Millan C, Balmaceda-Aguilera C, Castro T, Pastor P, Montecinos H, Reinicke K, Zuniga F, Vera J C, Onate S A, Nualart F. 2003. Hypothalamic ependymal-glial cells express the glucose transporter GLUT2, a protein involved in glucose sensing. *J Neurochem* 86: 709-24
61. Cheney L, Hou J C, Morrison S, Pessin J, Steigbigel R T. 2011. Nef inhibits glucose uptake in adipocytes and contributes to insulin resistance in human immunodeficiency virus type I infection. *J Infect Dis* 203: 1824-31
62. Lederer E D, Sohi S S, Mathiesen J M, Klein J B. 1998. Regulation of expression of type II sodium-phosphate cotransporters by protein kinases A and C. *Am J Physiol* 275: F270-7
63. Gekle M, Knaus P, Nielsen R, Mildenberger S, Freudinger R, Wohlfarth V, Sauvant C, Christensen E I. 2003. Transforming growth factor-beta1 reduces megalin- and cubilin-mediated endocytosis of albumin in proximal-tubule-derived opossum kidney cells. *J Physiol* 552: 471-81
64. Grosse-Hovest L, Hartlapp I, Marwan W, Brem G, Rammensee H G, Jung G. 2003. A recombinant bispecific single-chain antibody induces targeted, supra-agonistic CD28-stimulation and tumor cell killing. *Eur J Immunol* 33: 1334-40

What is claimed:

1. A pharmaceutical composition comprising:

(a) a protein comprising a first polypeptide or polypeptide domain having a first specific binding activity for Cytotoxic T-lymphocyte Antigen 4 (CTLA-4) expressed on a T-cell cell surface and a second polypeptide or polypeptide domain having a second specific binding activity for Glucose Transporter 2 (GLUT2) or an ectodomain thereof expressed on a pancreatic beta-cell surface, wherein the first and second polypeptide or polypeptide domain are independently an antibody molecule or a specific-binding fragment thereof, wherein binding of the first polypeptide or polypeptide domain to CTLA-4 induces a CTLA-4 specific agonist response in the T cell, and binding of the second polypeptide or polypeptide domain to GLUT2 or an ectodomain thereof does not inhibit GLUT2 glucose transporter function, wherein said agonist response in the T cell reduces immunoreactivity against pancreatic beta cells; and (b) a pharmaceutically acceptable carrier or adjuvant.

2. A method for preventing diabetes in an animal comprising the step of administering to the animal an effective amount of the pharmaceutical composition of claim 1.

3. A method for protecting pancreatic β-cells from autoimmune destruction in an animal comprising the step of administering to the animal a protective amount of the pharmaceutical composition of claim 1.

4. A method of producing Treg cells that down-regulate autoimmune responses to pancreatic β-cells in an animal comprising the step of administering to the animal an effective amount of the pharmaceutical composition of claim 1.

5. The method of claim 4 wherein the Treg cells are predominantly pancreatic tissue specific Treg cells and the autoimmune responses to pancreatic β-cells are mediated by pancreatic tissue specific T cells.

6. A method of producing immune tolerance to pancreatic β-cells in an animal comprising the step of administering to the animal an effective amount of the pharmaceutical composition of claim 1.

7. The method of claim 6, wherein the immune tolerance is pancreatic islet cell specific T cell tolerance.

8. A method for treating diabetes in an animal comprising the step of administering to the animal an effective amount of the pharmaceutical composition of claim 1.

9. A method for delaying development of diabetes in an animal comprising the step of administering to the animal an effective amount of the pharmaceutical composition of claim 1.

* * * * *